United States Patent [19]
Kramer et al.

[11] Patent Number: 5,280,265
[45] Date of Patent: Jan. 18, 1994

[54] STRAIN-SENSING GONIOMETERS, SYSTEMS AND RECOGNITION ALGORITHMS

[75] Inventors: James F. Kramer, Stanford; William R. George, San Francisco; Peter Lindener, Los Altos, all of Calif.

[73] Assignee: The Board of Trustees of the Leland Stanford Junior University, Stamford, Calif.

[21] Appl. No.: 625,305

[22] Filed: Dec. 10, 1990

Related U.S. Application Data

[63] Continuation-in-part of Ser. No. 258,204, Oct. 14, 1988.

[51] Int. Cl.$^5$ .............................................. H01L 3/06
[52] U.S. Cl. ................................. 338/210; 128/782
[58] Field of Search ...................................... 338/4–6, 338/210; 128/782

[56] References Cited

U.S. PATENT DOCUMENTS

| | | | |
|---|---|---|---|
| 4,311,980 | 1/1982 | Prudenziati | 338/4 |
| 4,348,634 | 9/1982 | David | 323/353 |
| 4,414,537 | 11/1983 | Grimes | 340/365 R |
| 4,542,291 | 9/1985 | Zimmerman | 250/231 R |
| 4,823,106 | 4/1989 | Lovell | 338/210 |
| 5,086,785 | 2/1992 | Gentile et al. | 338/210 |

OTHER PUBLICATIONS

Kramer, J., "Talking Glove", Proceedings Cal. State U., 1987.
D. E. Rumelhart, J. L. McClelland, and the PDP Research Group, Parallel Distributed Processing: Explorations in the Microstructure of Cognition, vol. 1, the MIT Press, Cambridge, Mass., 1986, pp. 318–330.
E. A. Wan, P. Ning, "Neural Tree Structured Vector Quantization" 1988, Stanford Report (short form).
J. Kramer, L. Leifer, "The Talking Glove: A Speaking Aid for Nonvocal Deaf and Deaf-Blind Individuals," Proc. 12th Ann Conf Rehabilitation Engineering (RESNA), pp. 471–472, New Orleans, La., 1989.
J. Kramer, L. Leifer, "A Talking Glove for Nonverbal Deaf Individuals," SIMA Tech Report, Apr. 1990, Stanford University.

Primary Examiner—David D. Knepper

[57] ABSTRACT

Goniometers are provided having internal compensation employing two opposing variable resistance strain sensing elements separated by a flexible film. The goniometers may be used in sets for detecting complex hinge or joint movements, where patterns of hinge or joint positions may be used to define symbols. Algorithms are provided for parsing values from a system of goniometers in motion having information content.

15 Claims, 32 Drawing Sheets

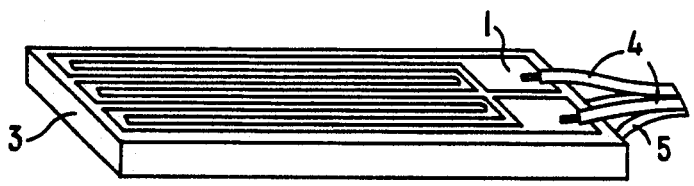
FIG. 12A
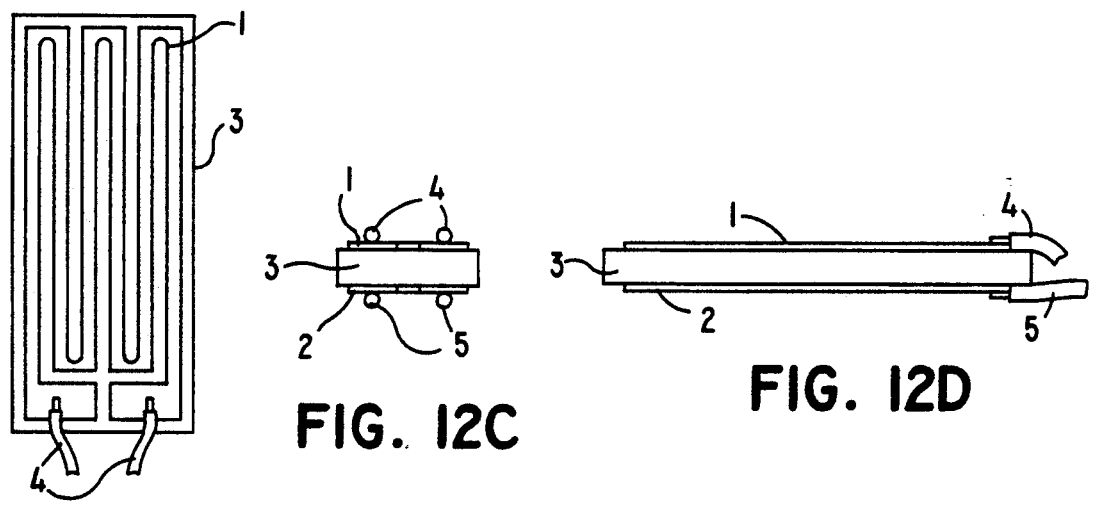
FIG. 12B  FIG. 12C  FIG. 12D
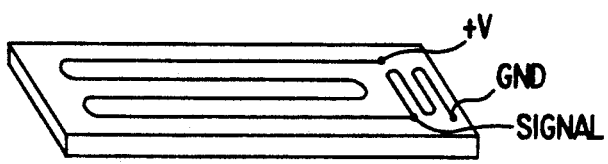
FIG. 13

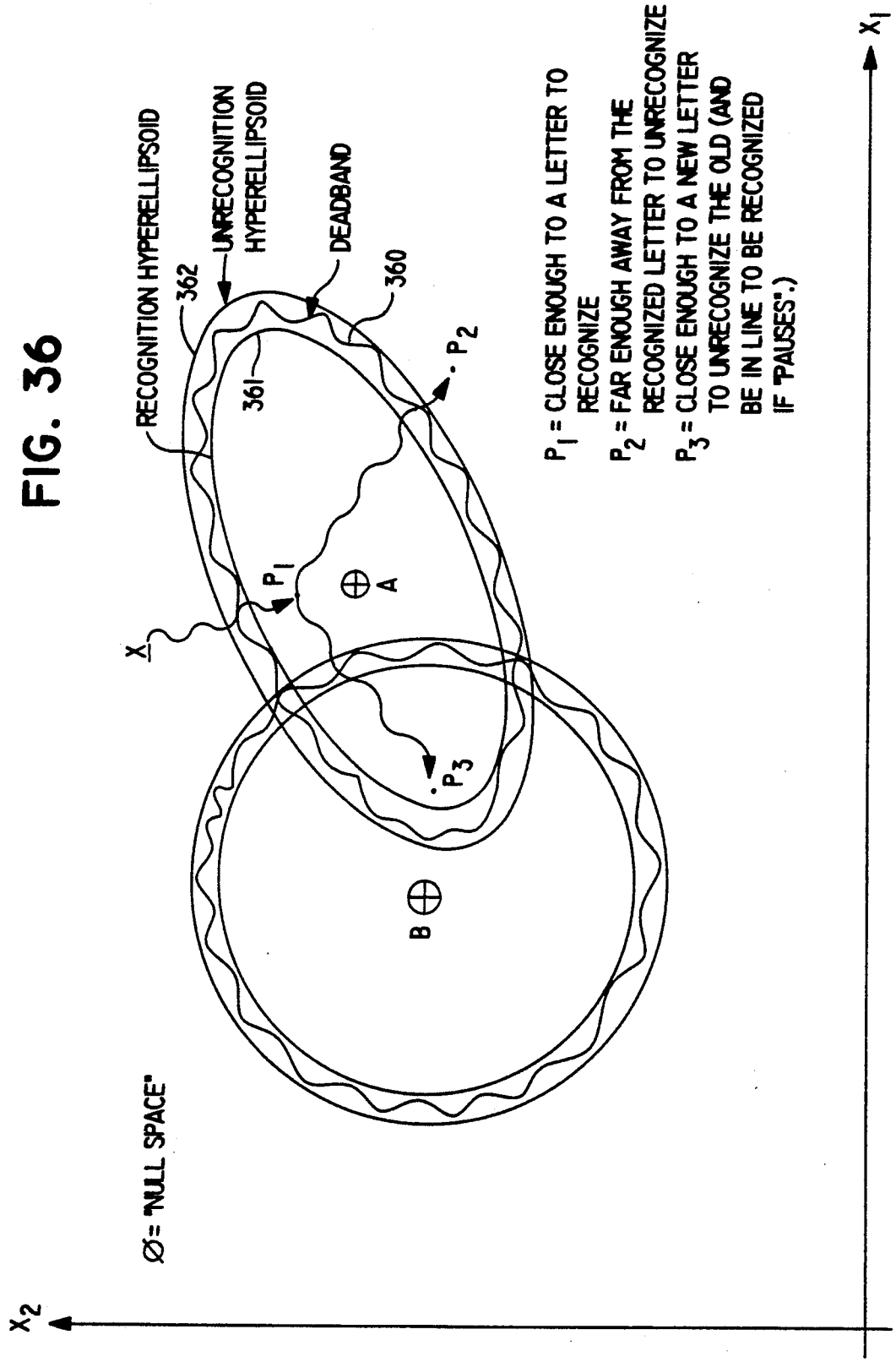

STRAIN-SENSING GONIOMETERS, SYSTEMS AND RECOGNITION ALGORITHMS

CROSS-REFERENCE TO RELATED APPLICATIONS

This application is a continuation-in-part of application Ser. No. 258,204, filed Oct. 14, 1988, which disclosure is incorporated in its entirety herein.

BACKGROUND

This invention relates to systems which sense spatial relationships and to the individual sensors used in the systems. The system is capable of producing a decision based on the values of one or more sensors. The system finds application in a variety of gesture recognition applications, exemplified by communication devices for nonvocal deaf or deaf-blind individuals. The system also finds application providing information on complex animate and inanimate motion which can be stored and/or processed immediately to construct a true or transformed model of the original motion. The model may be used to analyze the original motion or used as a control input to a second application.

There are various methods of sensing spatial relationships of interrelated parts, such as human and robotic joints and other moveable parts. In particular, there is a strong interest in improving on and developing new goniometric, i.e., angle measuring, devices. Commonly used goniometers, such as optical encoders, resolvers, potentiometers, Hall-effect sensors, and the like, are based on optical, electrical, mechanical and electromechanical technologies, etc. Most available goniometers are housed in bulky mechanical structures which can be difficult to mount and often interfere with the motion they are intended to track. The devices can be expensive, have limited resolution and can be difficult to use in a case where the bend axis is not rigidly defined and varies during flexure (e.g., a finger joint).

There is therefore a need for a low-profile, high resolution goniometer which is easily and unobtrusively mounted to a surface to monitor angles between two or more moveable structures associated with that surface (e.g., to monitor the bending of a joint or hinge, or the interrelation between the angles of a number of joints or hinges). The output of such a goniometer may be used to control the movement of computer generated objects or figures on a computer monitor, as well as to control the operation of physical machinery, and the like.

RELEVANT LITERATURE

U.S. Pat. No. 4,414,537 describes an instrumented glove which uses optical bend sensors, while U.S. Pat. Nos. 4,414,537 and 4,542,291 describe an instrumented glove using related optical sensing technology. Instrumented gloves are described by Foley, "Interfaces for Advanced Computing", Scientific American, October, 1987, pp. 127-135. A strain gage flex sensor is described in Jespersen, et al., "Joint Angle Position Sensor," 40th ACEMB, Niagara Falls, N.Y., Sep. 10-12, 1987, p. 104. A Hall-effect sensor used to measure finger joints is described in Marcus, et al., "Sensing Human Hand Motions For Controlling Dexterous Robots," 2nd Annual Space Operations Automation and Robotics Workshop, Wright State Univ, Jul. 20-23, 1988.

SUMMARY OF THE INVENTION

Sensors and sensor arrays are provided where each sensor is characterized by having at least one flexible variable resistance strain sensing element mounted to a flexible backing. In one embodiment the sensor motion is restricted by a guiding element and at least one end of the sensor is able to slide relative to the guiding element material. The guiding element is affixed to a surface and the sensor is guided by the guiding element to produce an electrical signal representative of the angle between two structures related to the surface. A plurality of sensors can be used to measure the conformation of the surface at a plurality of points.

Adaptive finger-gesture recognition algorithms are also provided where various pre-defined hand formations are recognized from continuously varying finger motion. Both a Bayesian and an artificial neural network classifier are described which select the appropriate gesture in conjunction with a dynamic gesture parsing routine.

BRIEF DESCRIPTION OF THE DRAWINGS

FIGS. 12a-d show views of the variable-resistance strain-sensing sensor.

FIG. 13 is a perspective view of a sensing array where one sensing element is not positioned parallel to the other.

FIG. 36 shows beacons in hand-space, with recognition and unrecognition hyperellipsoids.

DESCRIPTION OF THE SPECIFIC EMBODIMENTS

Figure 1:
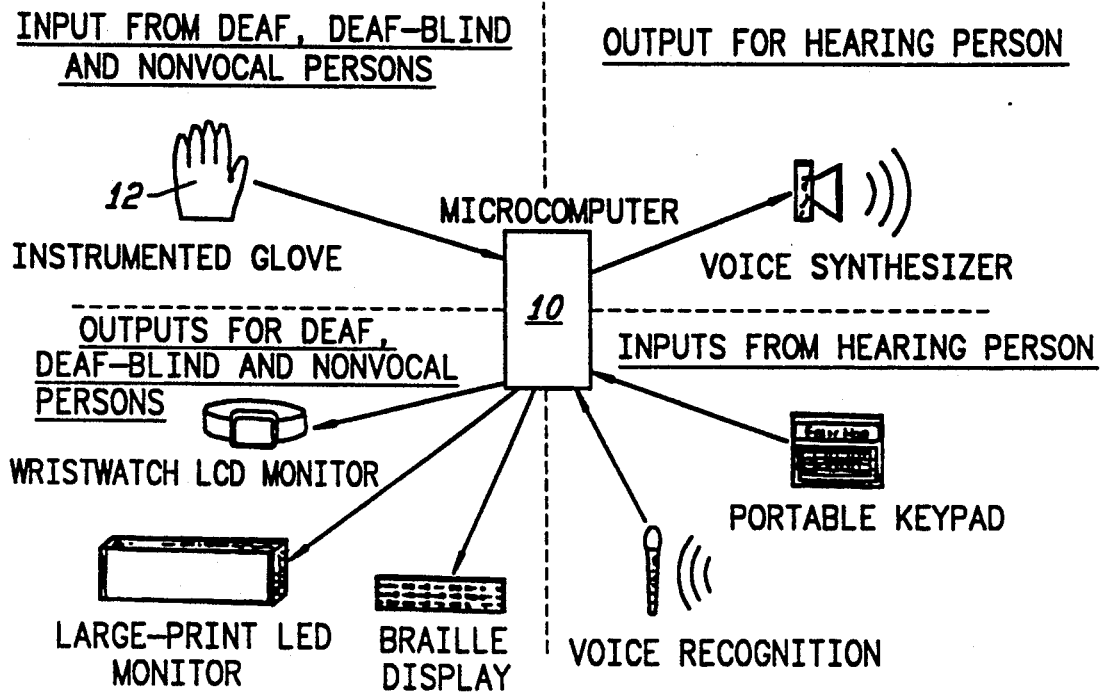
FIG. 1 is a functional block diagram of a communication system in accordance with the invention.

Sensor and sensor arrays are provided where each sensor is characterized by having a variable resistance strain sensing element (e.g., a strain gage) mounted to a flexible backing (FIGS. 12a-d). The sensor arrays comprise one or more (usually not more than two) variable resistance strain sensing elements 1 and 2. Multiple sensing elements are preferably mounted on opposite sides of the flexible backing 3 and attached by wires 4 and 5 to other circuitry. When mounted on opposing sides, the sensing elements are preferably positioned parallel to each other, but may also be positioned orthogonally (FIG. 13) or at other arbitrary angles.

Each sensing element consists of an electrically conductive material whose resistance varies with strain, such as metals and metal alloys, conductive inks (e.g., an adhesive impregnated with electrically conducting particles or fibers), semiconducting materials, conductive elastomers (e.g., an elastomer impregnated with electrically conductive particles or fibers), organic conductors, and the like. The material employed and the design of the sensor array preferably provides for a substantially linear response to changes in angle. The electrically conducting material is generally mounted to the flexible backing in a grid pattern, where the majority of the material is in strips along the perpendicular to the primary bend axis, thus, the sensor is relatively insensitive to bending along axes other than the primary axis.

The electrically conductive material for the strain sensing element is adhered to the electrically non-conductive flexible backing by adhesive, by casting the backing onto the electrically conductive material, by vapor deposition of the electrically conductive material onto the backing, or by other convenient means. The electrically conductive material is generally present as a thin film or foil strip, conveniently less than about two mils thick, but usually at least about 0.05 mil. The length of the sensing element will generally vary with the application, usually not less than one-quarter inch and not exceeding one foot. For example, the length of the sensing element ranges from about one-half to two inches for a glove or from about eight to ten inches for an elbow or knee. The width of the sensing grid will usually not exceed one-half inch, being about one-eighth inch for a glove and one-quarter to three-eighths inch for an elbow or knee sensor.

The backing material is conveniently an inert, low thermal expansion, flexible, electrically insulating, low mechanical hysteresis (i.e., due to bending) material, which may be a film, woven fabric, insulated metal or other supporting substrate with the appropriate physical and electrical characteristics. For the most part, plastic films find use, particularly films which may be cast. Films which may find use include polyimide, mylar, polypropylene, polyester and the like. The backing material will generally be of a thickness in the range of 0.2 to 10 mil, preferably from about 0.2 to 2 mil. With a thickness of an annealed nickel-copper electrically conductive material of about 0.1 mil, a polyimide backing of 0.5 mil is preferred for a glove.

When a single sensing element is adhered to a flexible backing, the backing is inelastic enough along the length dimension compared to the elasticity of the sensing element so that the sensing element is strained when the entire sensor assembly is flexed. When a sensing element is mounted to each side of a backing the relative elasticity along the length dimension of the backing is less critical. As long as during flexure of the entire sensor assembly the compression in thickness of the backing is negligible, the structure remains symmetric in cross-section and the neutral bend axis passes down the middle of the backing, thus one sensing element sees strain of equal magnitude but opposite sign to the other sensing element. This differential strain signal is ideal when used as input to a differential amplifier since not only is the desired signal resulting from bend of arbitrary angle doubled, but error terms introduced into the strain signal due to non-ideal or parasitic effects (e.g., change in temperature, electrical noise, mechanical hysteresis, changes in material properties due to aging or other ambient influences) are present in the signals from both strain sensing elements and thus their effects are reduced due to the common mode rejection of the differential amplifier.

Figure 14A:
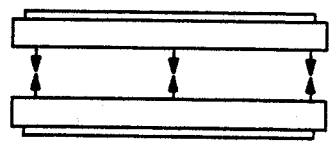
FIGS. 14A and 14B show one sensing element arrangement, and c and d show a second sensing element arrangement.
Figure 14B:
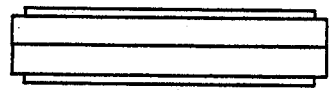
Figure 14C:
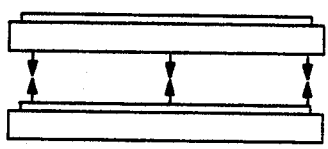
Figure 14D:
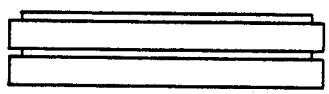

A number of individual sensors or an array of sensors may be fabricated together by affixing the electrically conductive strain sensing element to both sides of a piece of backing material and then etching both sides simultaneously to yield paired grids, i.e., one on each side of the backing material, where each pair of grids makes up an individual sensor. Similarly, a sensing element may be affixed to one side of a piece of backing material and then etched. Two mirror image etchings of the same array of sensors on separated backing sheets can be adhered together to produce grid pairs. When appropriately matched sheets of grid arrays are used, the two sheets may either be adhered backing material-to-backing material (FIGS. 14A and 14B) or backing material-to-grid side (FIGS. 14C and 14D). The latter would produce a thinner total backing thickness between the two matched grids. This method is used when production techniques makes it impossible to make a thinner single backing sheet. When both backings are adhered to each other a more symmetric structure is produced at the expense of doubling the total effective backing thickness.

Figure 5:
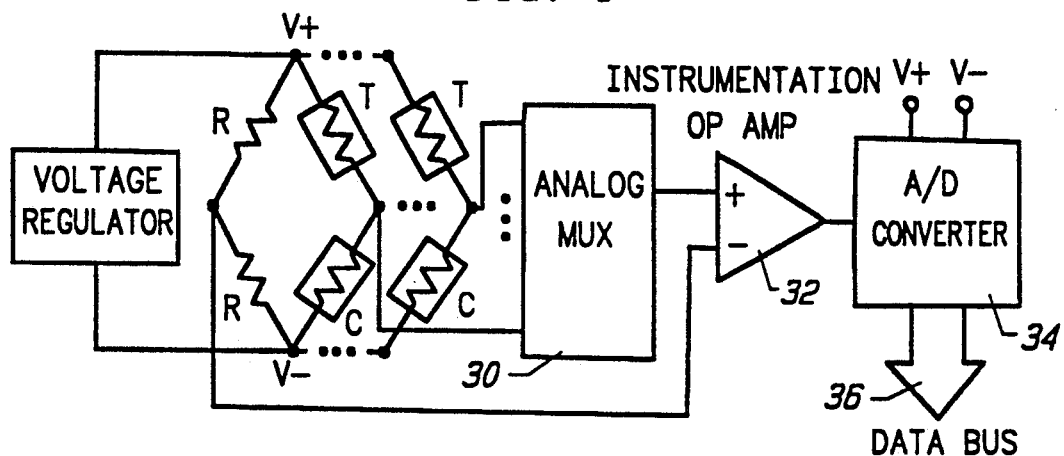
FIG. 5 is a functional block diagram schematic of a strain gage multiplexing bridge circuit for providing signals to the computer in the communication system of the invention.
Figure 15A:
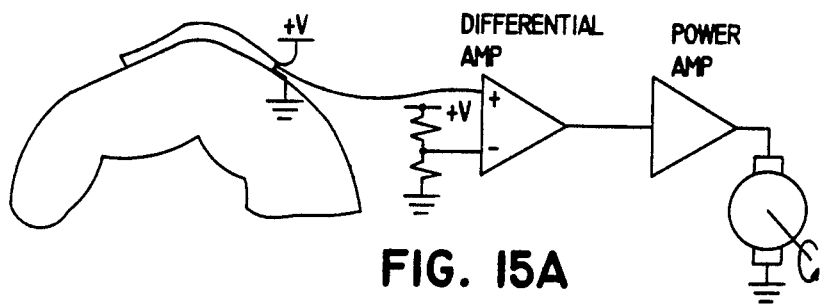
FIG. 15A shows the sensor signal processed by analog circuitry for use by an analog data utilization device.
Figure 15B:
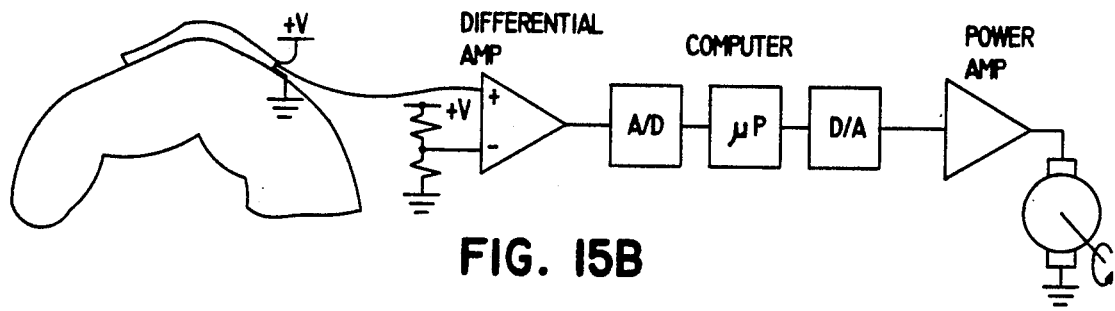
FIG. 15B shows the sensor signal processed by analog and digital circuitry for use by a digital data utilization device.
Figure 16A:
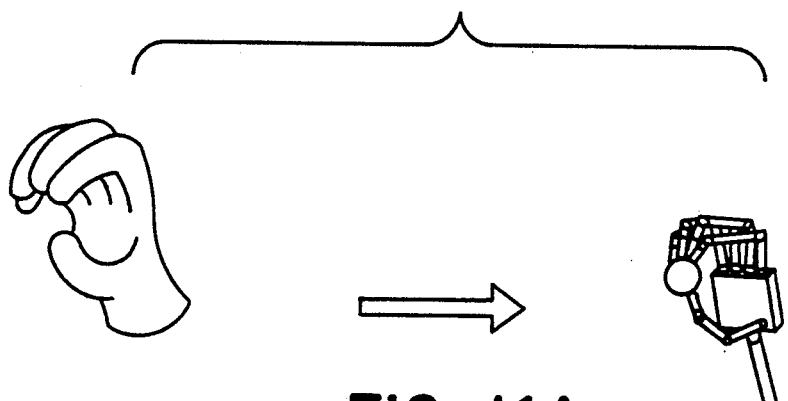
FIG. 16A shows the sensor signal controlling a robot gripper.
Figure 16B:
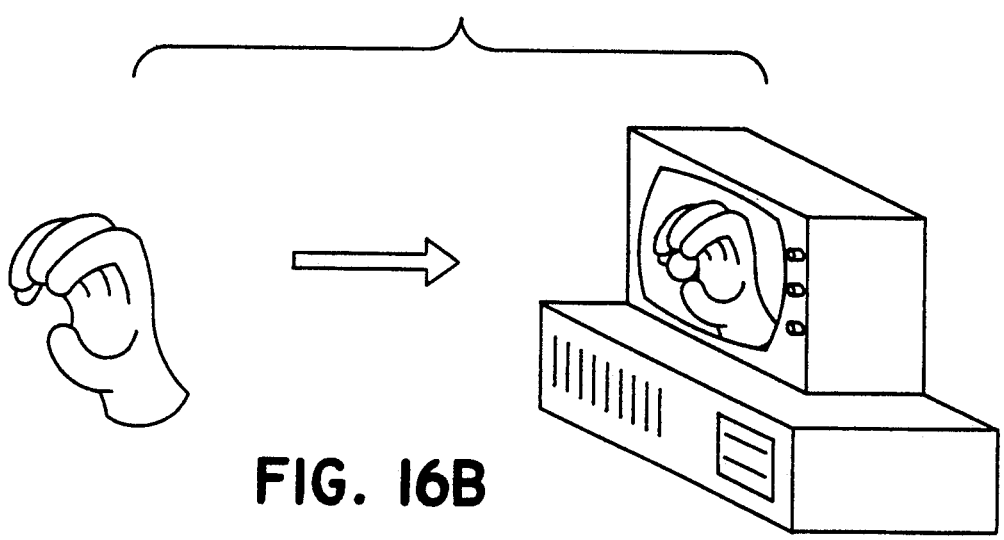
FIG. 16B shows the sensor signal controlling a graphic image.

The maximum strain seen by each sensor is adjusted by varying the thickness and elastic modulus of the plastic backing to which the sensor is mounted. The backing thickness and elastic modulus of the backing to which the foil is mounted. The sensors are preferably wired (4 and 5) in a Wheatstone bridge configuration that employs an analog multiplexer to select a particular strain sensor bridge voltage (FIG. 5). The analog signal from the sensor can be processed by analog circuitry (FIG. 15A) and used by an analog data utilization device, which may, for example, use the analog input in applications such as motor control (e.g., speed and position), control of an artificial limb (e.g., position and motion control), telerobotics (e.g., control of a remote robot manipulator or gripper, FIG. 16A), control of audio amplifiers (e.g., volume and tone), and the like. The analog signal can be converted to a digital signal for input to a computer or other digital data utilization device (FIG. 15B). Applications include, in addition to the analog applications mentioned above, positioning of a cursor (e.g., for use in CAD design or text editing), construction of a true or transformed graphic model (FIG. 16B) of the original motion (e.g., for use in Virtual Reality), recording of motion data for analysis and comparison (e.g., studying of human motion and flexibility), and the like. The transformed graphic model may take the form of a puppet, animated body part, animated character, animated form (e.g., a life form) and the like.

The total thickness of the entire sensor assembly is in the range of about 0.2 to 12 mil, where the total thickness of the annealed nickel-copper/polyimide sensor for an instrumented glove ranges from about 0.3 mil to 2 mil. The dimensions of the sensor and the nature of the materials used should allow the sensor to follow an angle of bending to preferably at least about $+/-115$ degrees.

The electrically conductive strain sensing element of the sensor assembly is connected to amplification and data processing circuitry by electrically conducting means, such as lead wires, electrical traces (etched or deposited), and the like. For typical applications requiring one or more portions of the body to be instrumented, typical lead-wires range from 26 to 36 AWG, are comprised of stranded wire and have a flexible insulation. For an instrumented glove, 36 AWG stranded copper Teflon-insulated wire may be used.

There are many applications for the subject sensors where a single sensor may be employed or groups of sensors may be combined and applied in various manners. Included among the applications are measuring body (e.g., finger) movements, bending of hinges, travel of conveyor or timing belts and other flexible surfaces, contoured surfaces, angle of bend of cantilevered structures, axial rotation and the like.

Figure 17:
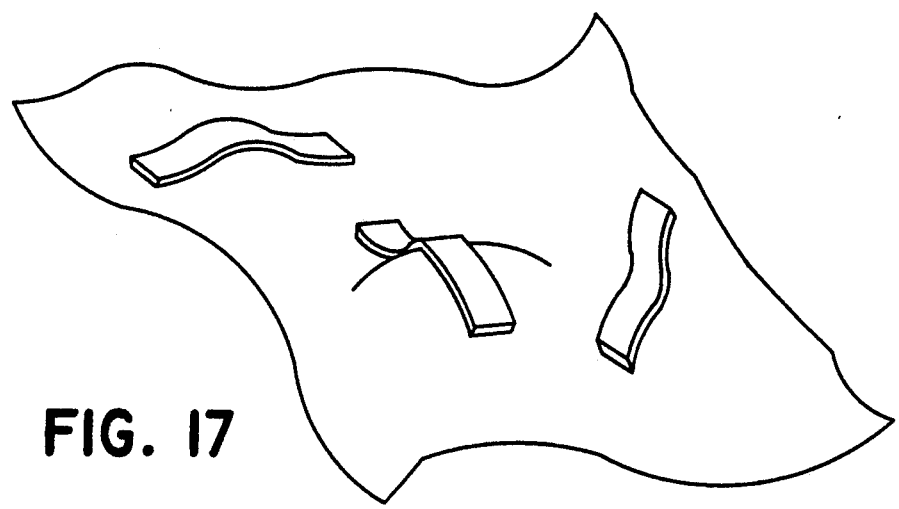
FIG. 17 is an application for the subject sensor in measuring surface contours.
Figure 18:
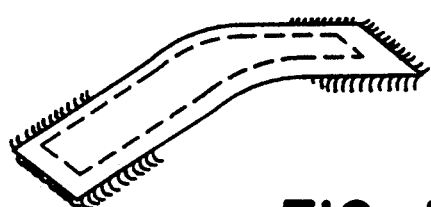
FIG. 18 shows a sensor in one type of guiding element.
Figure 19:
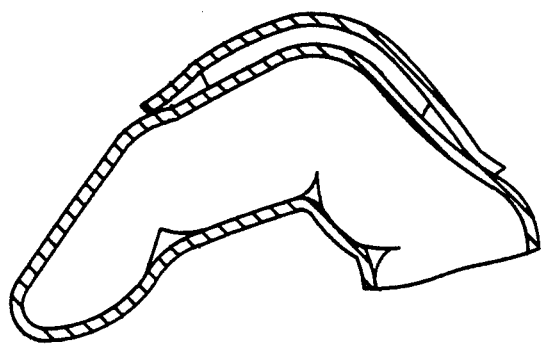
FIG. 19 shows a sensor in a guiding pocket.

In using the subject sensors for following body or surface contours (FIG. 17), a film, fabric or other material is employed which closely follows the flexible joint or surface to be measured. With a hand, the fabric may be formed in the form of a partial or whole glove. With other parts of the body, the fabric may be formed as a knee or ankle brace, vest, suit or the like. The fabric will conform to the contour of the surface and hold the sensing element in close juxtaposition (FIG. 4) to the surface making the sensor able to measure changes in the conformation of the surface. The sensor may be mounted onto or over the surface in a guiding element (FIGS. 4,18,19,20). The guiding element may take the form of a pocket in which the sensor may reside (FIGS. 18,19). The sensor may freely move within the constraints of the guiding element, may be affixed at one end with the other end free to move (FIG. 20), may be affixed at both ends with slack in the sensor between the ends, or may be affixed to the glove material where the glove material is elastic and stretches when the sensor flexes (e.g., the sensors may be molded directly into a ubber or plastic material).

Of particular use for the sensors is the use of a plurality of sensors in a glove (FIGS. 3,21,22) for providing electrical signals related to movement of the hand and fingers. The glove is equipped with sensors as described above, which monitor the angles of the finger joints. At least a portion of the sensor resides in a guiding channel to guide the sensor relative to the joint as the joint is flexed. For example, the guiding channel may comprise one or more loops through which the sensor passes (FIG. 20) or the sensor may be completely enclosed in a pocket and affixed over each joint to be monitored (FIGS. 18,19).

Figure 21:
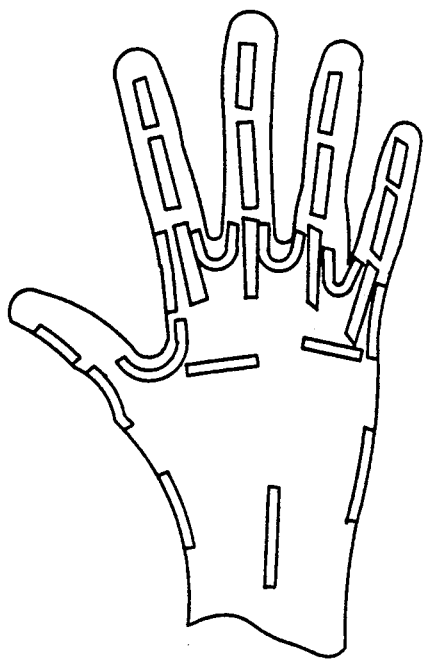
FIG. 21 shows the subject sensors located at desirable locations on the hand.

The sensors can be placed at various locations in relation to the joints of the hand, for example by affixing the guiding channels or pockets onto a glove or sewing the pocket directly into or onto the glove. Typical bend sensor locations are over the metacarpophalangeal, proximal and distal interphalangeal joints of the four medial fingers and trapeziometacarpal, metacarpophalangeal and interphalangeal joints of the thumb (FIG. 21).

Figure 24A:
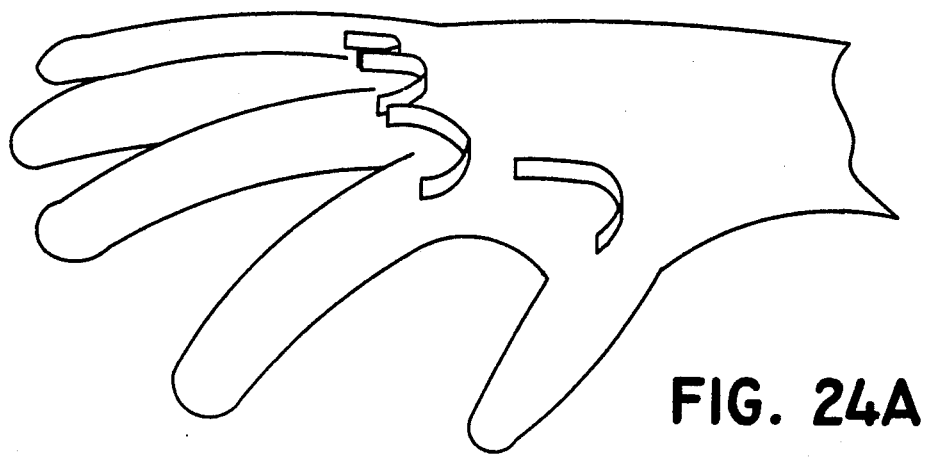
FIGS. 24A and 24B are sensors shaped in a "U" to measure joint abduction.
Figure 24B:
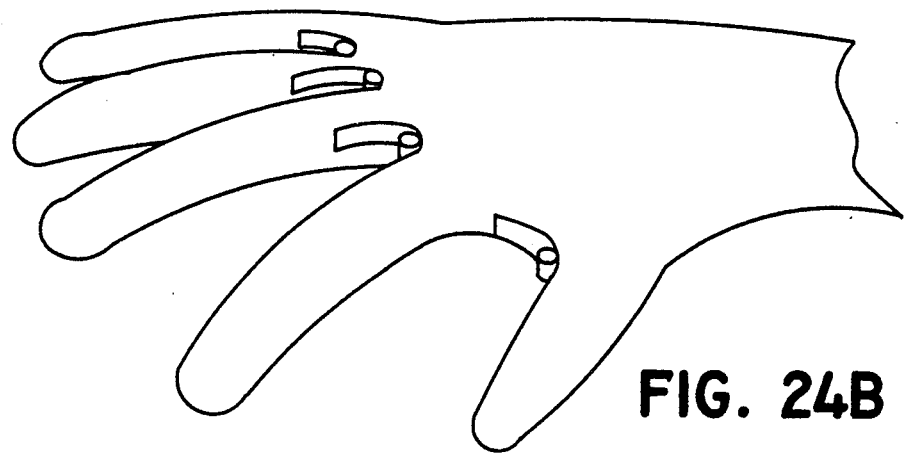
Figure 25A:
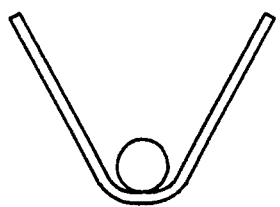
FIGS. 25A-25D are bend-limiting elements.
Figure 25B:
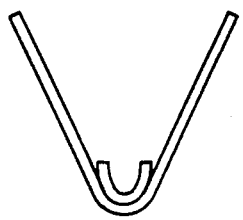
Figure 25C:
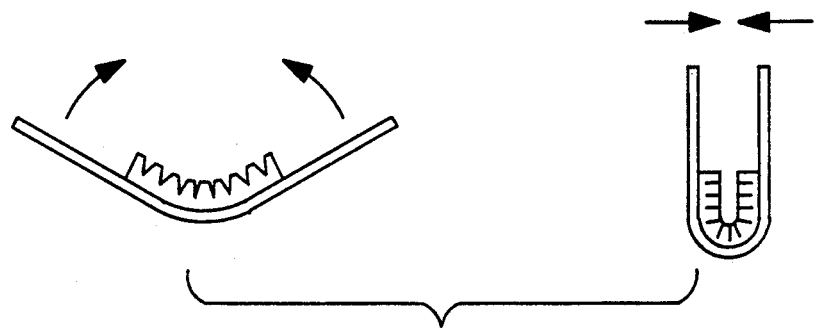
Figure 25D:
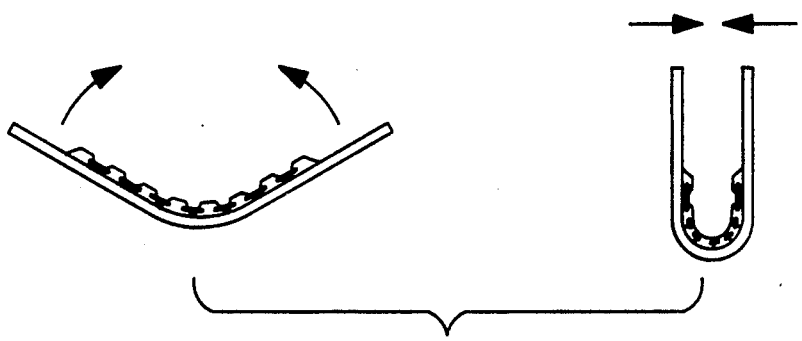

Abduction sensors may be used and in particular are used to measure the abduction of the metacarpophalangeal joints of the four fingers and the trapeziometacarpal joint of the thumb. As with the sensors in general, the abduction sensors may reside in guiding pockets, may be free to slide, affixed at one or both ends, or be affixed to an elastic glove material (e.g., molded into a rubber or plastic material). "Absolute" abduction sensors may be located on the side of the index and small fingers (FIG. 21,23b, 23c) or positioned on edge on the dorsal side of the hand near the abducting joint (FIGS. 23A, 35A-35C). "Relative" abduction sensors may be located between any neighboring pair of digits, particularly near the metacarpophalangeal joints to measure the angle between the digits. The relative abduction sensor may take on a U-shaped configuration and may be positioned between two digits in the abduction plane (FIG. 24A) or located on the dorsal surface of the hand (FIG. 24B) above the abduction plane. When a U-shaped relative abduction sensor is located in the abduction plane a bend-limiting element is preferably placed between the joints near the sensor to prevent the sensor from being bent beyond the minimum bend radius (and from being creased). The bend-limiting element may take the form of a tube (FIG. 25A), half tube (trough, FIG. 25B), flexible structure which suddenly binds and becomes stiff at the desired bend radius (FIGS. 25C,25D), and the like. Additional sensors measure the rotation of the thumb across the palm and the arch of the metacarpus near the small finger. FIG. 21 shows sensors on the back of the metacarpus to measure the thumb rotation and metacarpal arch near the small finger. Sensors may also be placed on the top and side of the wrist to measure pitch and yaw of the wrist in relation to the forearm (FIG. 21).

Figure 22A:
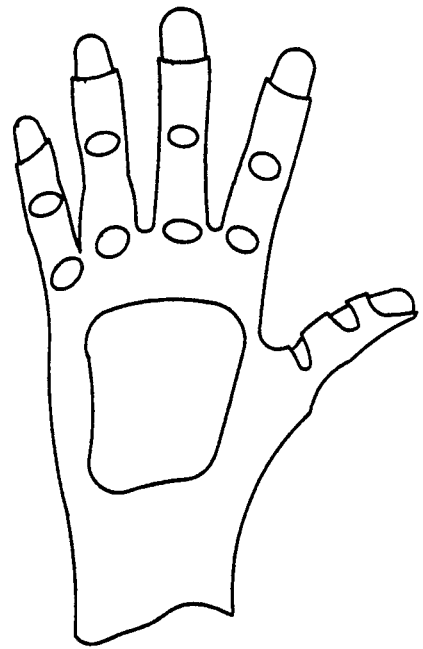
FIGS. 22A and 22B are two gloves with portions of the gloves removed or replaced with mesh.
Figure 22B:
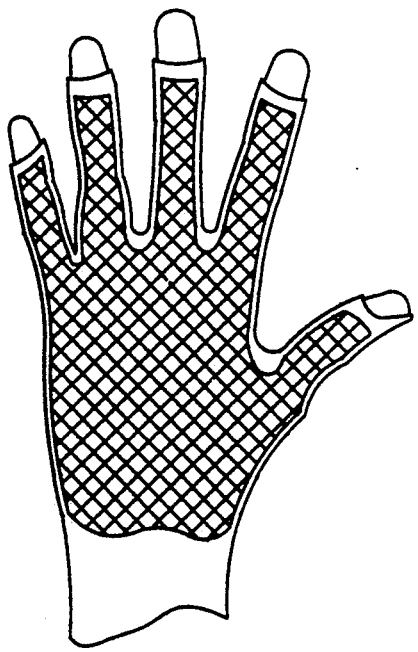
Figure 23A:
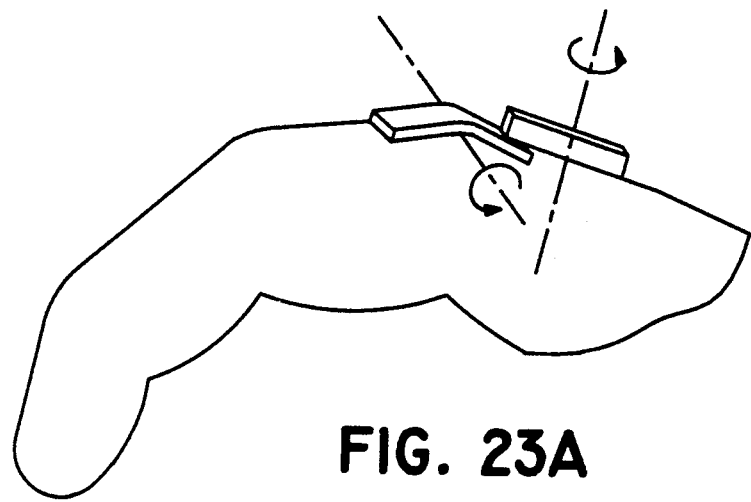
FIGS. 23A-23C are three techniques for using the subject sensor to measure joint abduction.
Figure 23B:
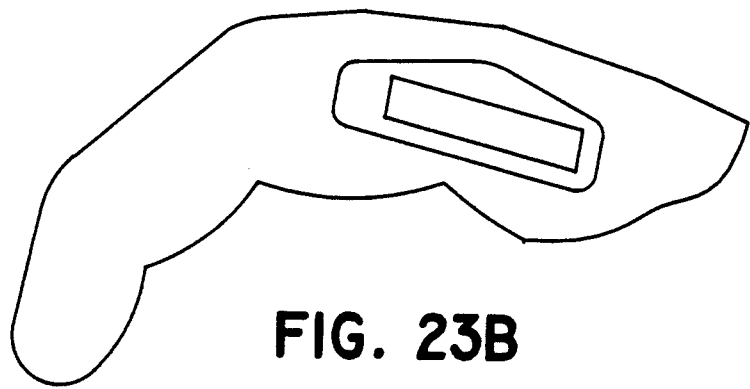
Figure 23C:
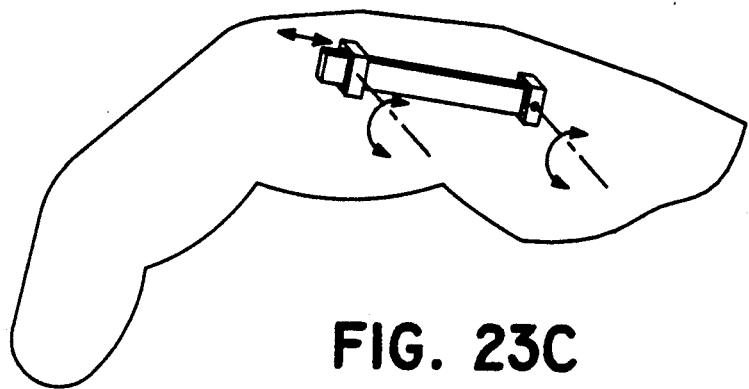
Figure 26:
FIG. 26 is a glove where the fingertip material is removed.

The fingertips of the glove are preferably removed (FIGS. 22,26) to permit the user to reliably grasp objects when it is not necessary to measure the flexure of the outer finger joint (distal interphalangeal joint). Material covering any knuckle on the palm side of the glove, as well as a large portion of material covering the palm, may also be removed to prevent binding and provide ventilation (FIG. 22A). Elastic mesh material (FIG. 22B) may be used to replace portions of the fabric to provide greater comfort and ventilation and to help decouple one sensor from another due to tension through the fabric from movement of an adjacent joint.

Figure 27A:
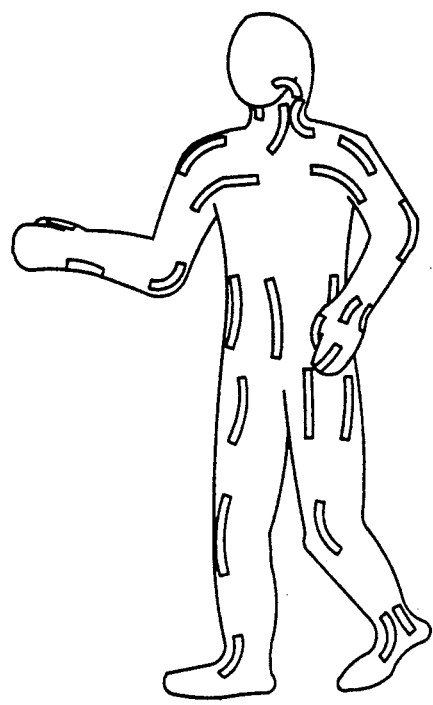
FIGS. 27A and 27B show the subject sensor located at various locations on a body.
Figure 27B:
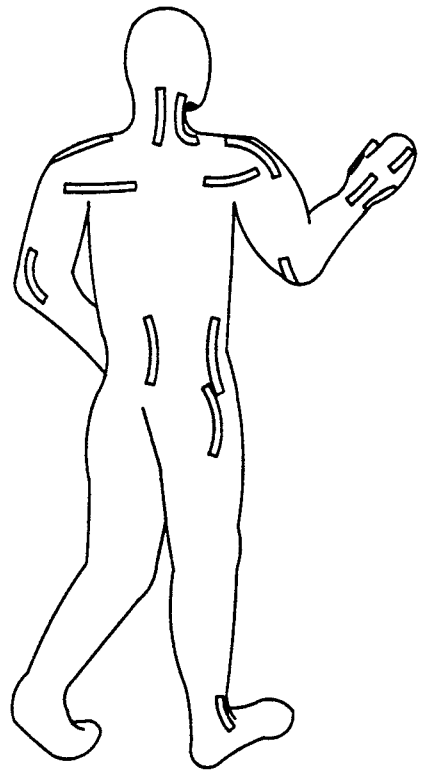
Figure 28:
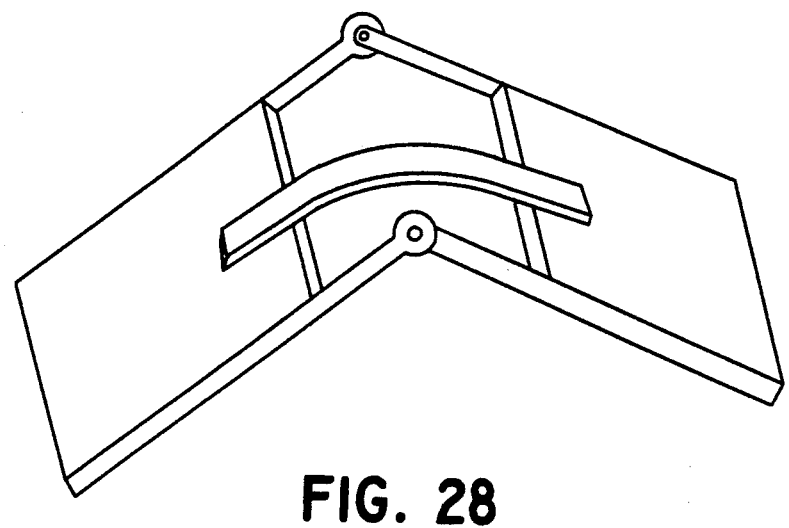
FIGS. 28 and 29 show a sensor attached to hinged structures.

For other body parts, the bend and abduction sensors will be employed in a manner similar to the glove embodiment. The sensors are long enough to span the entire are subtended by the angle being measured. The guiding pocket may be an integral part of or affixed to a tubular elastic housing which is placed around the joint or region to be monitored. Areas which may be monitored include ankle, waist, elbow, back, neck, wrist, shoulder, hip, groin, knee, or other flexible region (FIGS. 27A,27B).

Figure 20:
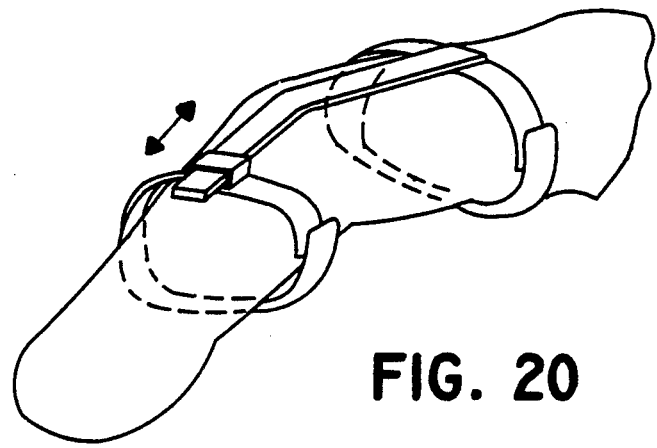
FIG. 20 shows a sensor guided by a channel.
Figure 29:
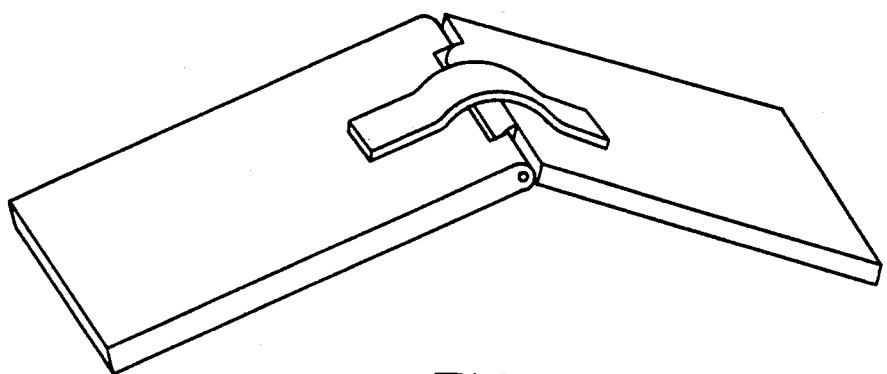
Figure 30A:
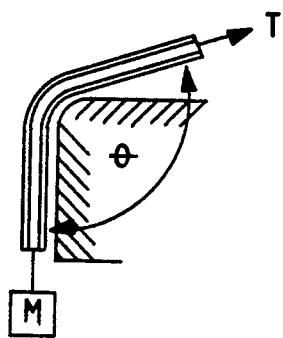
FIGS. 30A and 30B show the subject sensor used to simultaneously measure angle and tension.
Figure 30B:
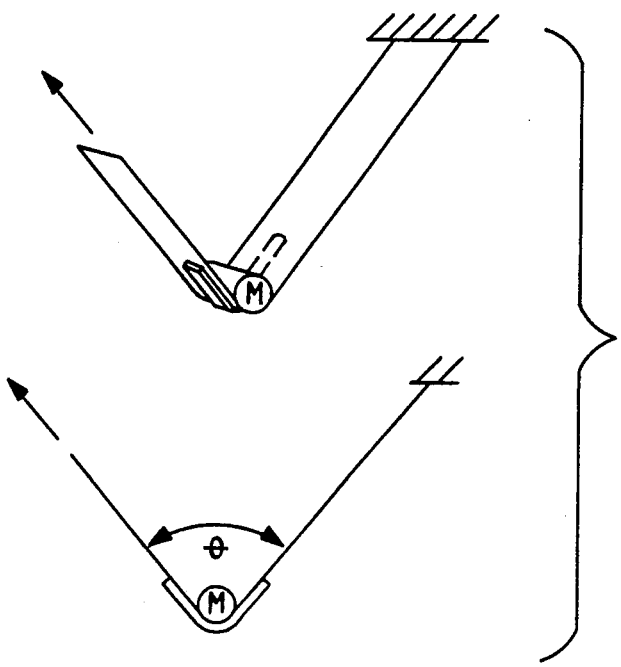
Figure 31:
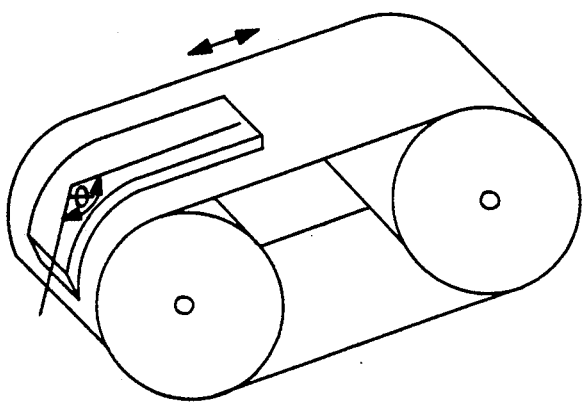
FIG. 31 shows the sensor measuring the position of a pulley belt.
Figure 32:
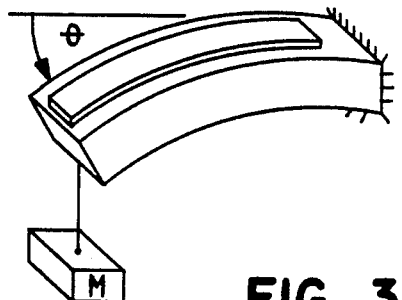
FIG. 32 shows the sensor measuring the bend of a cantilever specimen.
Figure 33:
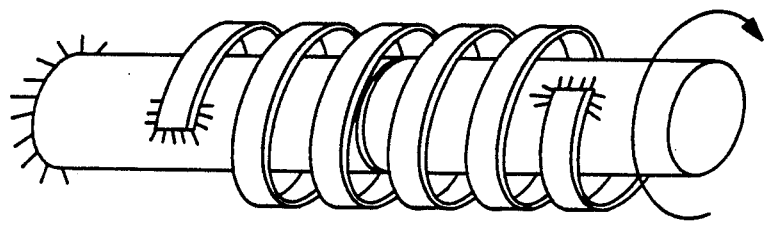
FIG. 33 shows the sensor measuring axial rotation.
Figure 34A:
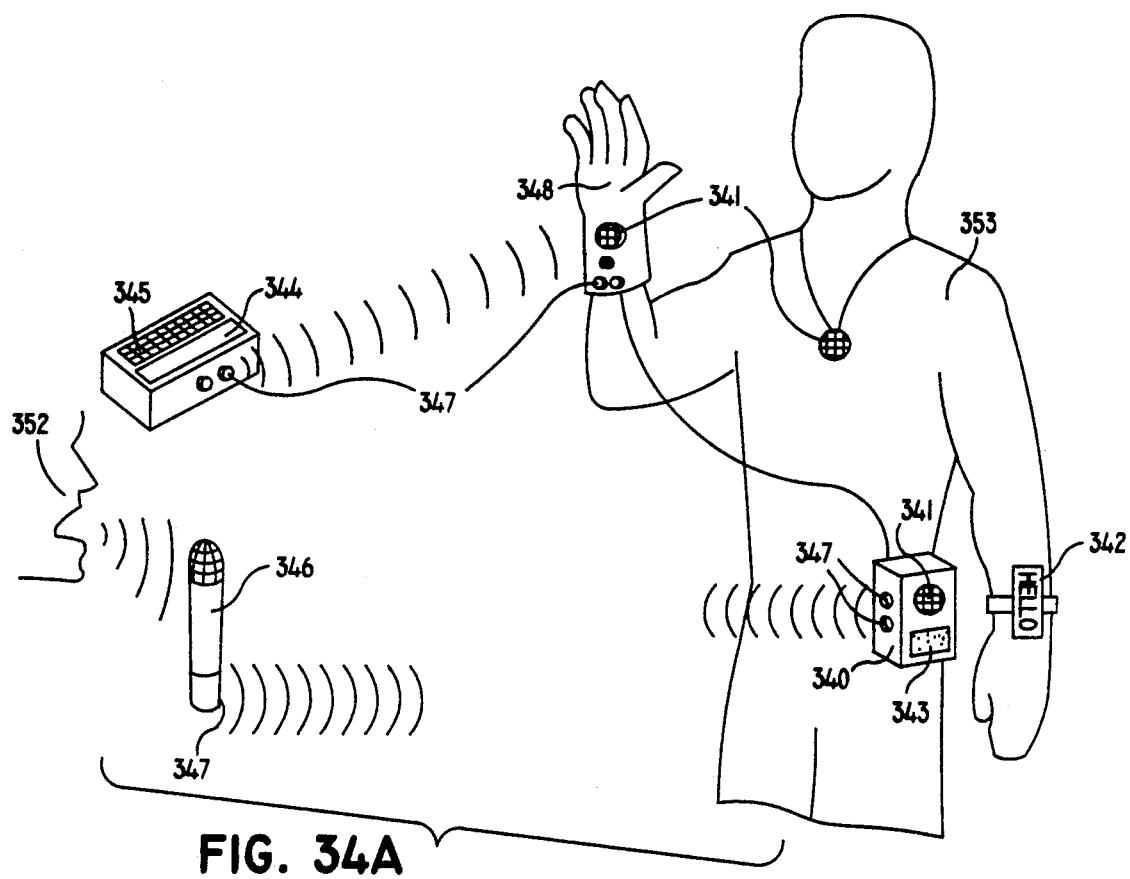
FIG. 34A shows an instrumented glove being used with various additional peripheral and communication devices in a communication system, where a gesture recognition algorithm is used capable of producing symbolic output and control signals, including synthesized speech.
Figure 34B:
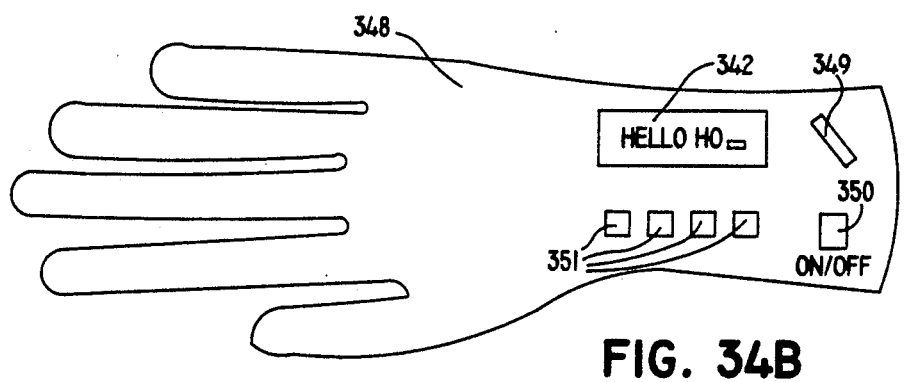
FIG. 34B provides the dorsal view of an instrumented glove and FIG. 34C provides the palmar view of the glove.
Figure 34C:
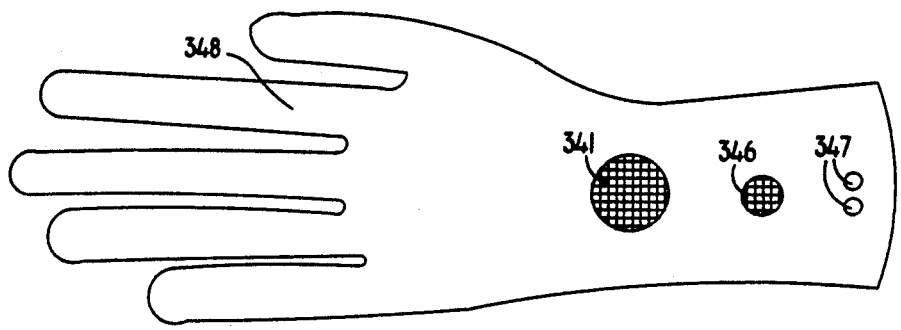
Figure 35A:
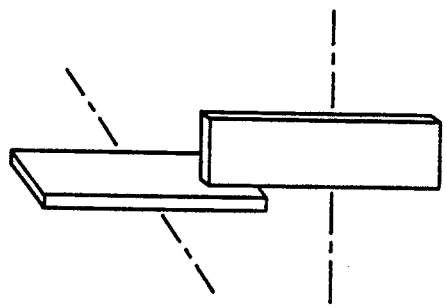
FIGS. 35A-35C show three views of a configuration for measuring joint abduction.
Figure 35B:
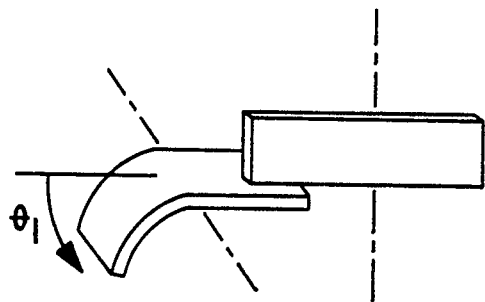
Figure 35C:
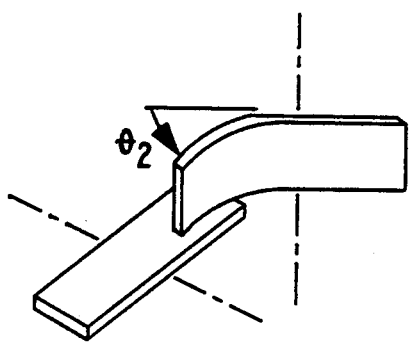

Sensing applications for other than body parts allow for variations in structure from the measurement of body parts. For example, with hinge structures having one or more hinges along the same axis with a separation in between, the sensor may be firmly affixed to the structure on each hinge member, extending through the separation (FIG. 20). In another embodiment employing a single hinge structure (i.e., without a separation between two or more hinges, FIG. 29) the sensor may be affixed at both ends on opposite sides of the hinge with a loop in between or other slack, such that the sensor can extend over the hinge during flexure without stretching and tearing. At no time need the sensor be taut and the sensor is configured so that it should not be completely extended. Where one wishes to simultaneously measure flexure and tension (FIGS. 30A, 30B), the ends of the sensor may be affixed to the tension producing element, where the differential signal from the two sensing elements represents the angle of the sensor and the common mode signal from the two sensing elements is representative of the tension applied to the sensor. The sensor may also be used to measure the position of the pulley belt by affixing the sensor to the pulley belt near the region where the belt is in contact with the pulley (FIG. 31). As the pulley turns and the belt is bent around the pulley, the sensor will also be bent producing a signal indicative of the pulley belt position. One may also use the subject sensors in conventional ways by adhering the sensor to a specimen, which is to be bent e.g. a cantilever beam (FIG. 32). By use of the subject sensor, the adherence of the sensing assembly to a flexible specimen is not as critical as when mounting a strain gage directly to the specimen, as is conventionally done, since it is only important that the sensing assembly remain in juxtaposition to the flexing specimen surface. When a coiled sensor structure is used (FIG. 33), the sensor may be used to measure axial rotation and changes in angles greater than 360 degrees.

A data utilization device is employed with the sensor(s). The data utilization device selected varies depending on the application of the sensors, the number of sensors involved and the information output desired. As described above, the strain-sensing elements comprise half-bridges in a Wheatstone bridge amplifying circuit (FIG. 5). The output from multiple half-bridges may be multiplexed and compared to a reference half-bridge voltage by a differential instrumentation amplifier. The analog output voltage may be processed by analog signal processing circuitry and used by an analog data utilization device. For example, the output voltage from a joint bend sensor may be amplified and filtered and used to control the velocity and/or position of a joint servo motor controlling a slave device (FIG. 15A).

Alternately, the output voltage may be digitized by an analog-to-digital converter and input to a microprocessor or other digital data utilization device for further processing (FIG. 15B). The digitized sensor value may be used in various monitoring and control systems. For example, joint flexure may be recorded both before and after an operation to monitor the rate and level of recovery of the joint or limb. The digitized sensor value may also be used in a digital feedback system to control the angle of an arcuate surface.

Where a plurality of sensors are involved, and the relative relationship of the sensors is determined, as in a glove 348 used for the determination of the position of a plurality of joints, a computer, which is preferably portable 340 and carried by the user (FIGS. 1, 2, 34A-34C), receives the digitized glove sensor data from the analog-to-digital converter and transforms the information into symbolic output, e.g., letters and control signals based on a finger gesture recognition algorithm, which can, for example, recognize fingerspelled letters. For nonvocal individuals, the glove and recognition algorithm may be used with a voice synthesizer and other various peripheral devices to produce a "speaking" communication device (FIGS. 1, 2, 34A-34C). As each spelled letter is recognized, it may be displayed for a sighted glove-user on a visual text display 342 (e.g., an LCD screen worn as a wristwatch) or for a deaf-blind glove-user on a portable braille display 343. Spelled words are then communicated to another person by a speaker 341 or visual display 344 or sent to another glove-user's visual or braille feedback displays.

Other inputs to the computer system may be provided for communicating with the glove user 353. In the case of a hearing impaired user, a hearing person 352 can reply by typing on a miniature keyboard 345 or by speaking through a microphone 346 into a voice recognition system. As before, if the hearing impaired user is sighted, the response from the hearing person may be displayed on a visual text display 342, and if the hearing impaired person is also visually impaired, the response may be displayed on a braille feedback device 343.

To help prevent random hand motions from being incorrectly recognized as letters, the glove may include an orientation and/or position sensor 349 (such as a mercury tilt switch or electromagnetic orientation and position sensor) to disable the recognition when the hand is not in a desired orientation or position. The system and/or glove may also have an on/off switch 350 to disable the recognition routine or various other functions. The system and/or glove may have additional function control switches 351.

The various input/output devices can be hard-wired to the computer, but the devices are preferably interconnected with the computer by an infrared link 347 or other non-wired transmission means.

In addition to a braille display in the case of a deaf-blind individual, other various tactile feedback devices may be employed such as vibrotactile displays (e.g., the Opticon TM piezoelectric tactile stimulator), electrocutaneous stimulators and robotic hands (e.g., a mechanical fingerspelling hand, U.S. Pat. No. 4,074,444). The robotic hand may be used in direct telerobot mode, i.e., a joint sensor value of the glove is processed and used to control a corresponding joint of the robotic hand (FIG. 16A), or a hand-pose may be recognized using the glove with the finger-gesture recognition algorithm (i.e., the adaptive pattern recognition algorithm) and this hand-pose mapped to some appropriate robotic hand configuration (which may be exactly the same as the glove user's hand pose or different being defined by the configuration of the hand-pose).

The communication device configuration described above may be used to aid multiple individuals to communicate over the telephone. When the glove is used in direct telerobotic mode (FIG. 16A) a deaf-blind person "reading" the robotic hand is able to sense mood and personality of the glove-user to whom he/she is communicating since the robotic hand is capable of mimicking subtle finger motions. Similarly, a sighted deaf person could view the robotic hand output or a graphic hand model (FIG. 16B) being controlled by the glove-user to whom he/she is talking. Using the glove to control a graphic hand for telephone communication has an advantage over simply sending a video image of the real hand in that due to the present bandwidth limitations of telephone lines (i.e., 300-3000 Hz) a full graphic image cannot be sent and updated real-time. The image of the hand must be data-compressed, sent, then uncompressed and redisplayed on the other end of the phone line. The uncompressed image is normally not of good visual quality. However, using a glove, only the important joint motion information is sensed and sent across the telephone line. This joint information is used to quickly construct a graphic hand model for viewing.

Figures 2A, 2B:
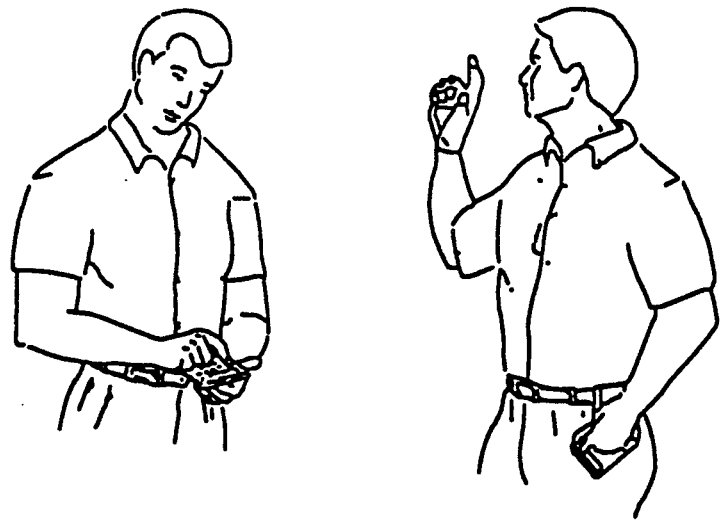
FIGS. 2A and 2B illustrate a hearing person and a deaf-blind person communicating with a communication system in accordance with the invention.

An earlier embodiment which was found to be satisfactory is described in the following figures. Referring now specifically to the drawings, FIG. 1 is a functional block diagram of a communication system in accordance with the invention and FIGS. 2A and 2B illustrate a hearing person and a deaf-blind person communicating using the system. The system provides expressive and receptive communication capabilities for deaf, deaf-blind and nonvocal persons. Although the preferred embodiment of the system is portable, as shown in FIG. 1, some components of the present prototype (FIG. 7) are too large to be carried.

The prototype system consists of a Motorola 68HC11 microcomputer board, with various interchangeable peripheral devices that encode and display information. Each user can select the peripheral devices that best satisfy his individual communication needs. In the Figures, the arrows denote the directions of information flow.

As shown in FIG. 2B, a non-vocal deaf-blind user is transmitting synthesized speech to a hearing person. The non-vocal person fingerspells while wearing a glove equipped with uniquely designed strain gage flex sensors. The microcomputer receives finger joint angle information from the instrumented glove 12 (FIG. 1, upper left). The microcomputer executes a letter recognition algorithm based on the joint angle information.

The recognition algorithm selects the most probable letter from an array of prestored hand formations that characterize the user's fingerspelling "signature." Once the letters of a word have been recognized and stored, a read-out command is given and the entire word is spoken to the hearing person (FIG. 2A) via a DECtalk speech synthesizer. The non-vocal individual wears a small output speaker (FIG. 1, upper right) as a "speech pendant" under his shirt. In effect, the non-vocal person's information output device is a "talking glove." After each word is spoken, the recognition algorithm adapts itself to reduce sensitivity to ongoing variations in letter formation and sensor placement.

Figure 11A:
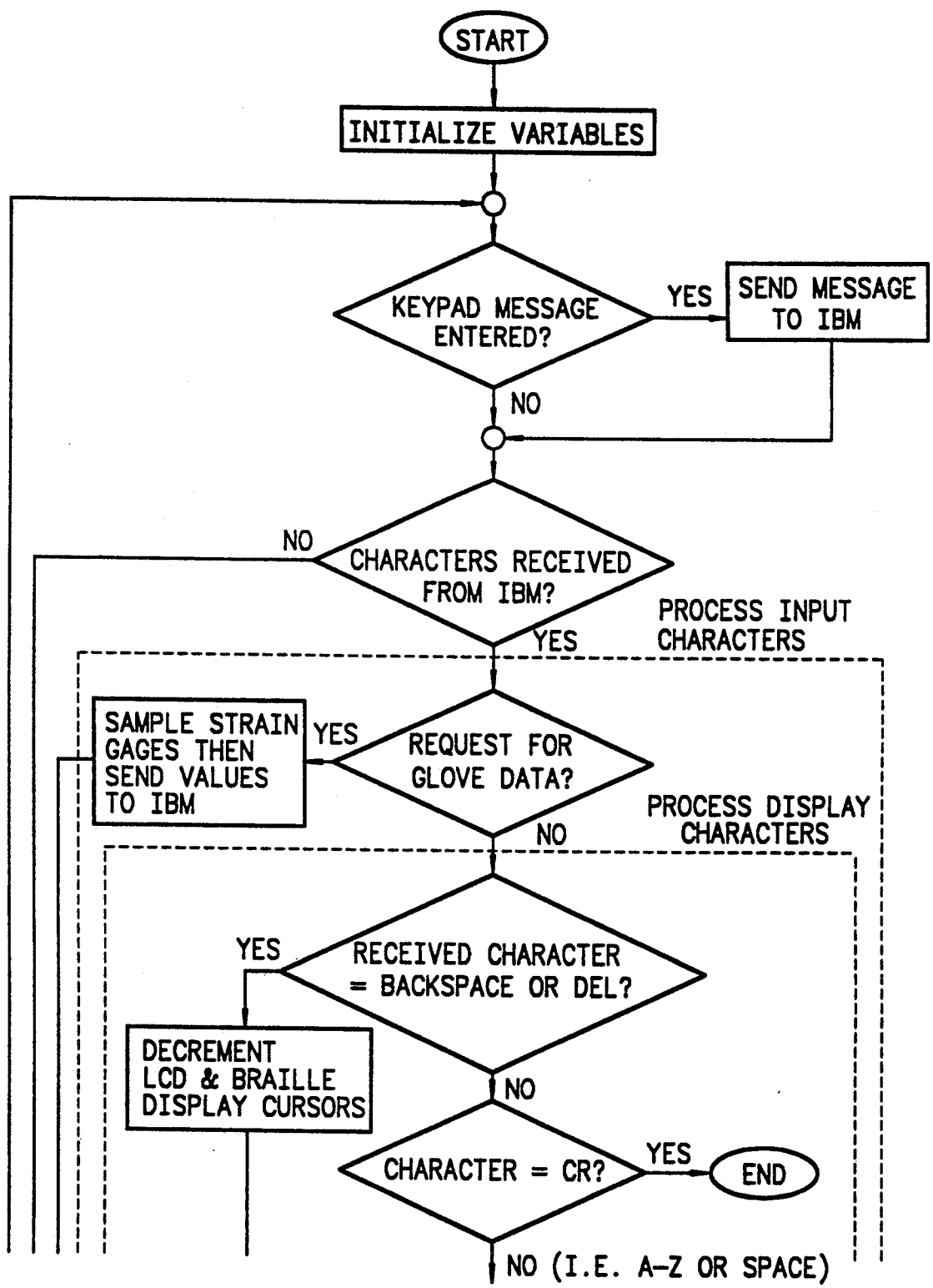
FIG. 11 is a flow diagram of an I/O and sampling software routine in the system of FIG. 7.
Figure 11B:
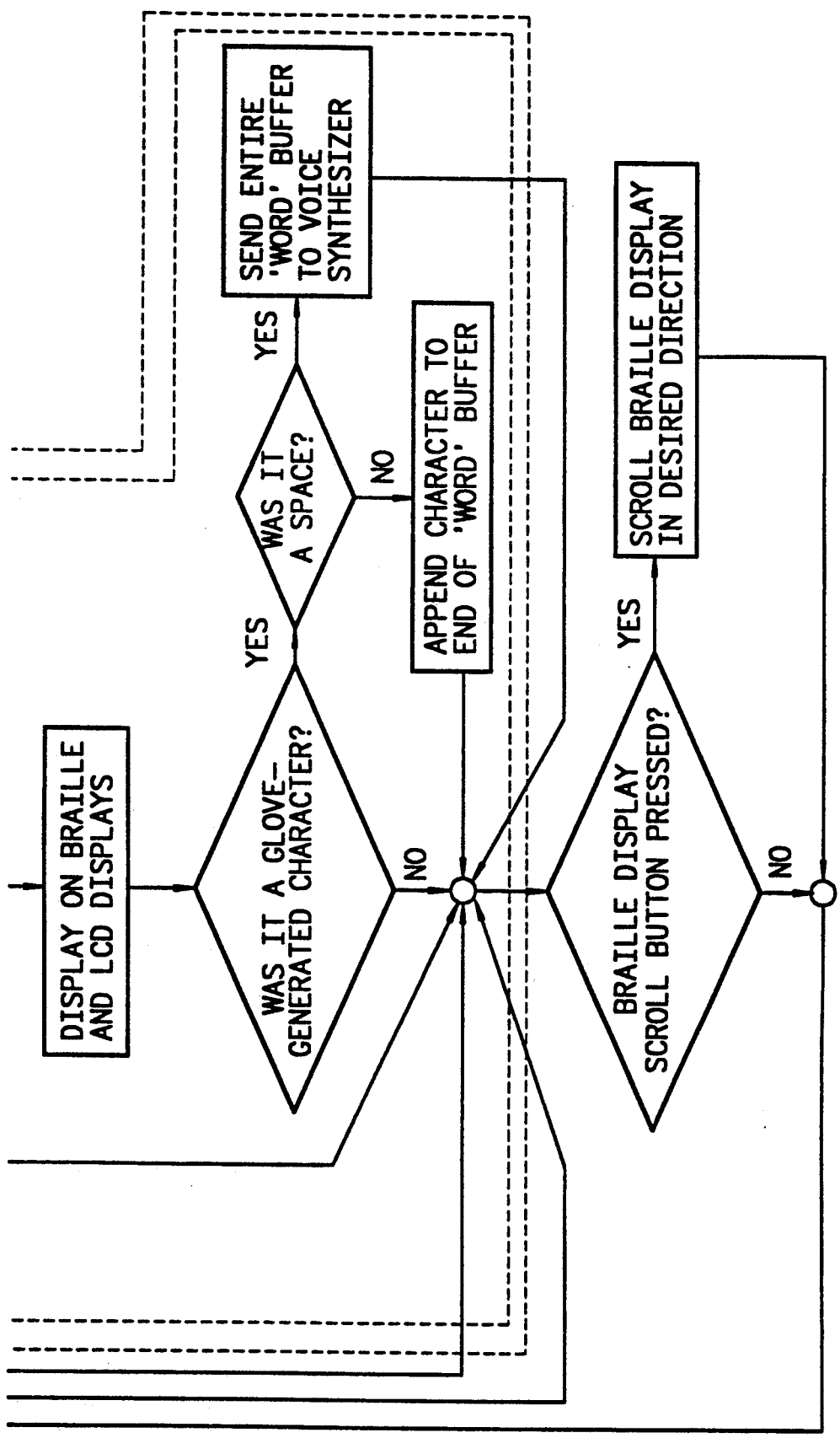

A hearing person replies to the deaf user by typing on the keyboard of a Radio Shack pocket computer (FIG. 11, lower right and FIG. 2A). The keyboard has a wireless link (infra-red) to the microcomputer so it can be carried in the shirt pocket of the deaf or deaf-blind individual and handed to the hearing person. The small keyboard has a liquid crystal display (LCD) that states the deaf person's name and requests message input from the hearing individual. Data entered on this keyboard is transmitted to the microcomputer and displayed for the deaf person using one of the methods described below. It is possible for several keyboards and microcomputers to share a common communication channel so that more than one hearing individual could participate in the same conversation with more than one deaf or deaf-blind person.

An IntroVoice voice recognition system can be integrated for use in certain structured environments, such as at home or at work. Individuals trained on this system can speak directly to the deaf individual. Their speech is detected by a small, directional microphone (incorporated into the deaf person's speech pendant) and converted into text by the vice recognition equipment (FIG. 1, lower right)

Text generated by the hearing person, using either the pocket keyboard or voice recognition system, is displayed for the deaf individual in a variety of ways (FIG. 1, lower left). For sighted deaf persons, the entered message is displayed on a small Seiko LCD monitor work like a wristwatch. For def persons with reduced vision, text can be output on a high-visibility large- character LED display. For a deaf-blind user, information is presented on a specially designed mechanical braille display (FIG. 2B). The braille display can fasten to the belt for use while walking and standing but detach for desk-top use. Braille displays can also include a calculator mode, and a data-bank function to record names, phone numbers and appointments.

Figure 3:
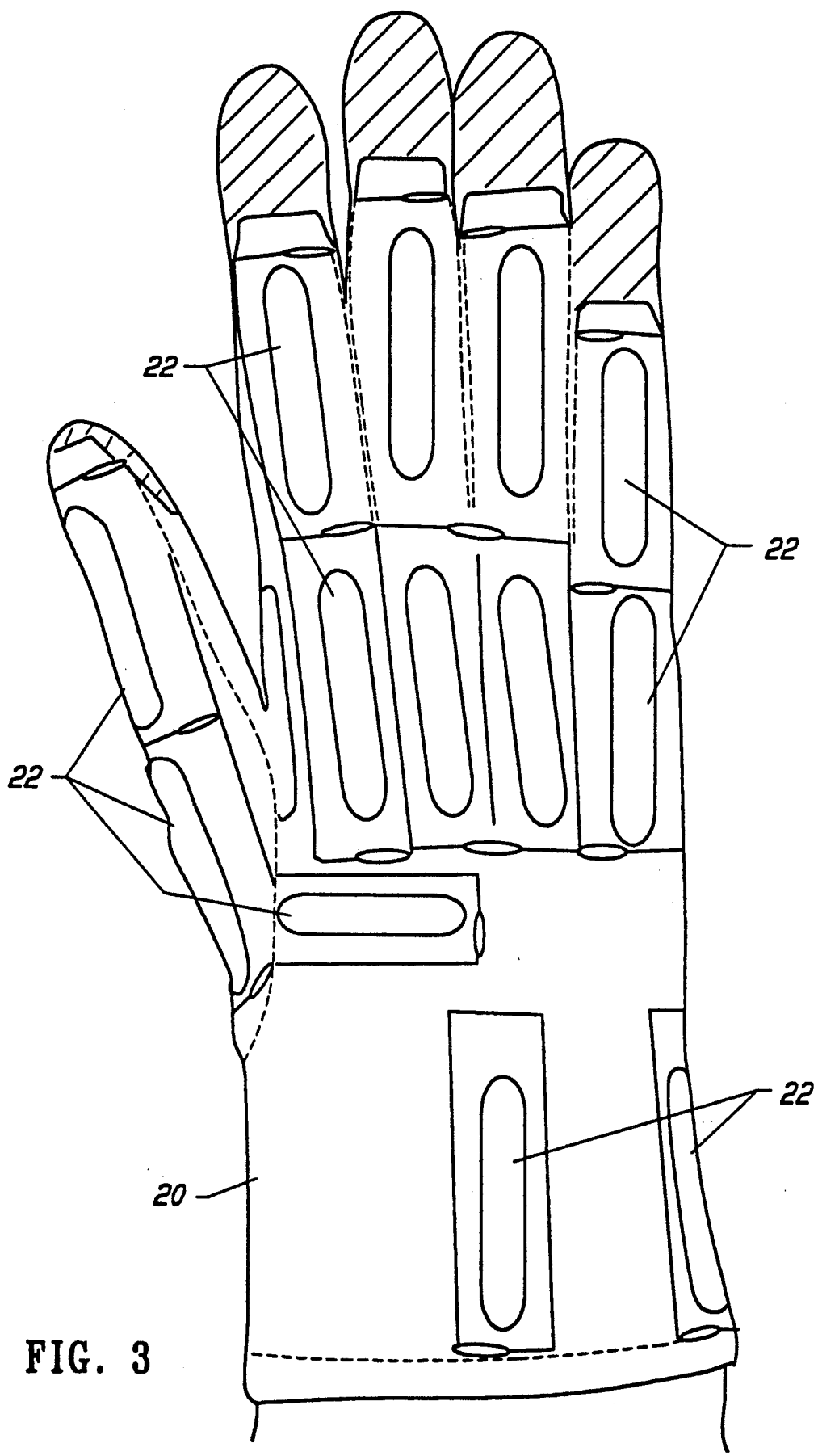
FIG. 3 is a plan view of an instrumented glove in accordance with one embodiment of the invention.
Figure 4:
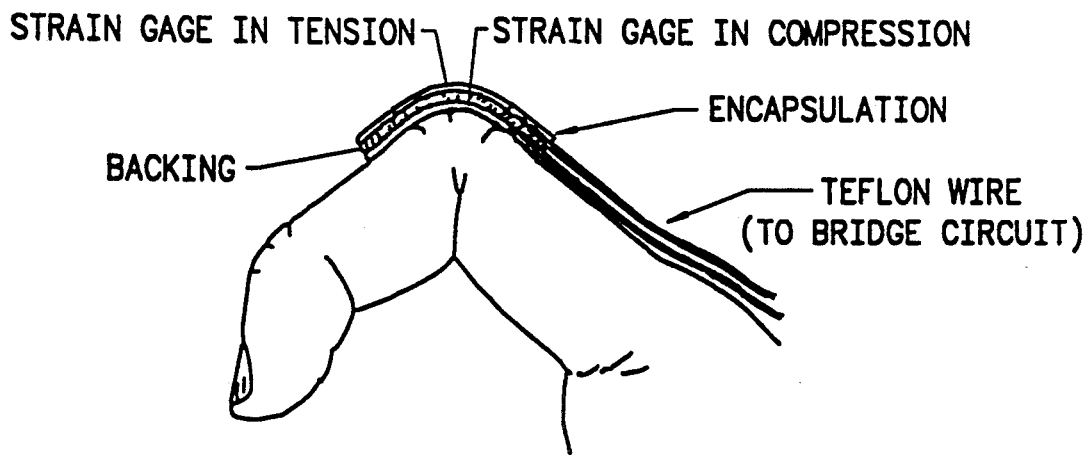
FIG. 4 is a side view of a finger joint and a strain gage flex sensor as used in the glove of FIG. 3.

FIG. 3 is a plan view of a glove 20 in accordance with one embodiment of the invention. The glove has fourteen strain gage sensors inserted into pockets 22 sewn in the glove, to sense joint flexure of the fingers while fingerspelling letters. FIG. 4 is a side view of a finger and a strain gage sensor for sensing the flexure of the finger joint. In accordance with one embodiment, two strain gage resistors are mounted on a 1 mil polyimide backing material so that during flexure, one strain gage is in tension while the other strain gage is in compression. A 120 ohm high elongation annealed Constantan resistor strain gage from Microengineering II (model PAHE-DF-750-120 LEN) has been used.

Data from the joint sensors is used by an adaptive pattern recognition algorithm to identify the intended letter from the fingerspelling hand formation. Recognized letters and phrases can also be sent to other devices such as a TDD or computer. In effect, the user's information output device is a "talking glove."

The instrumented glove is attractive and comfortable. The fingertips and palm of the glove preferably are removed to increase functionality and ventilation. Exposed fingertips permit the user to reliably grasp such objects as a pen or coffee cup, while the open palm allows a deaf-blind person to accept manual fingerspelling. Material covering the middle knuckle on the palm side of the glove can also be removed to prevent binding. As noted above, each angle sensor consists of two long flexible strain gages mounted back to back. The strain gage assembly resides in a guiding pocket sewn over each joint. The maximum strain seen by each gage is adjusted by varying the thickness and elastic modulus of the plastic backing to which the gage is mounted. The backing thickness is selected to maximize the output signal without significantly reducing the fatigue life of the gage.

The gages are wired in a Wheatstone bridge configuration that employs an analog multiplexer to select which bridge voltage is to be sampled by an analog-to-digital converter, as illustrated in FIG. 5.

Each sensor has a pair of strain gages, one in tension (T) and one in compression (C), which are used with fixed resistors (R) in a Wheatstone bridge arrangement. Each sensor bridge output is multiplexed through MUX 30 (AD7506, for example) to amplifier 32 (AD624, for example). The voltage offset of each input to MUX 30 can be varied by an offset potentiometer (not shown). The output of amplifier 32 is then applied to A/D converter 34, and the digital output from converter 34 is applied through bus 36 to the computer. The voltage range of the input to A/D converter 34 can be selected by choosing the appropriate gain of amplifier 32.

The core of the control software is an adaptive pattern recognition algorithm. In the algorithm, each sensor value is treated as one component of an overall "hand-state vector," i.e., each joint angle represents one axis in an n-dimensional "hand-space" where n is the number of instrumented joints (typically n=14). As the hand moves, the hand-state vector traces a trajectory through hand-space. This is shown for a three-dimensional space in FIG. 6.

Figure 6:
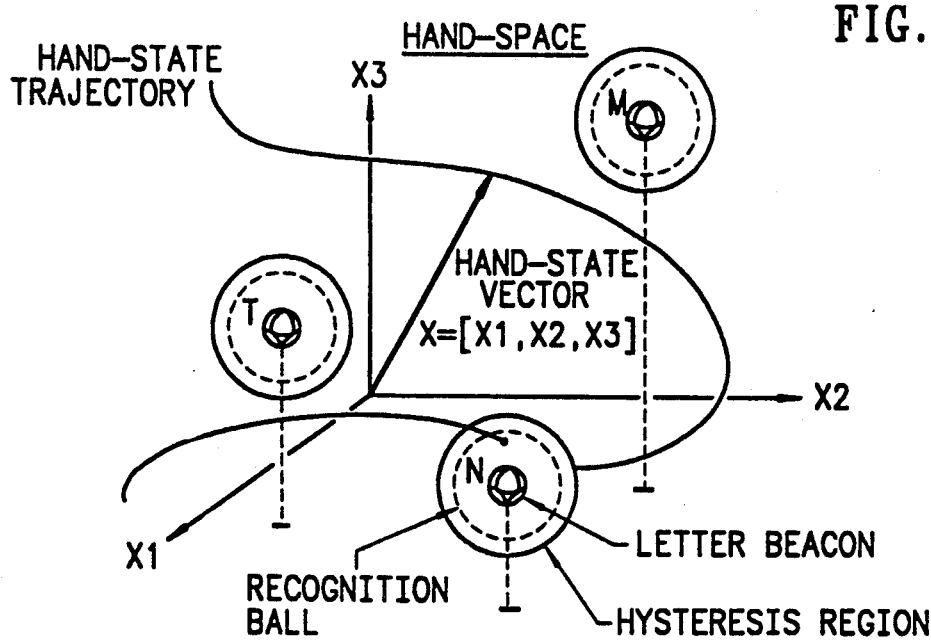
FIG. 6 is a hand-space diagram for a three-dimensional space illustrating a hand-state vector and three letter beacons as identified by a letter recognition algorithm in accordance with a feature of the invention.

Initially, sensor information must be stored for each letter to inform the system of the user's fingerspelling "signature." The sets of stored sensor values are represented figuratively by "letter beacons" in hand-space (FIG. 6). When the algorithm detects a reduced hand-state velocity, a letter formation is suspected, and the nearest beacon is determined. If the instantaneous hand-stage lies within the closest beacon's "recognition ball," denoted figuratively by the dashed inner spheres in FIG. 6, the corresponding letter is recognized and placed in a work-assembly buffer. To avoid unintentional repeated recognition of the same character, hysteresis is introduced into the letter identification algorithm by requiring that the hand-state vector leave the outer sphere before a new character is determined. Backspacing is permitted, and a "say it" beacon exists which, when recognized, causes the letters in the work-assembly buffer to be spoken by a DECtalk voice synthesizer. When a word is spoken, the letter beacons are adaptively updated to reflect their new, most probable positions in hand-space. Continuous adaptation reduces sensitivity to ongoing variations in letter formation and sensor placement.

Figure 7:
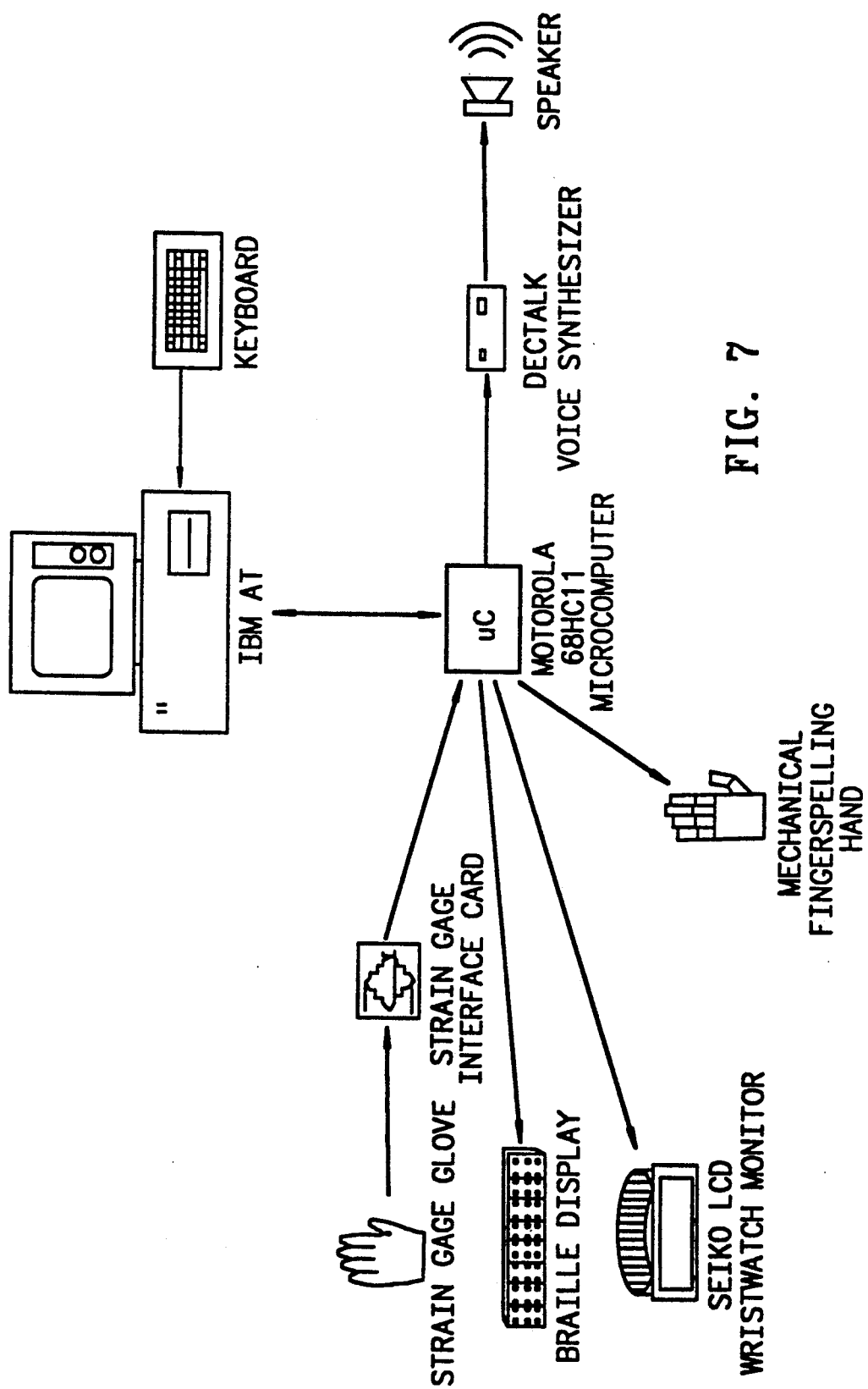
FIG. 7 is a functional block diagram of a prototype system developed at Stanfor University.

FIG. 7 is a functional block diagram of a prototype communication system developed at Standford University in which the recognition algorithm is implemented in an IBM AT personal computer. A Motorola 68HC11 microcomputer communicates with the IBM AT and also controls the operation of the peripheral devices.

Figure 8A:
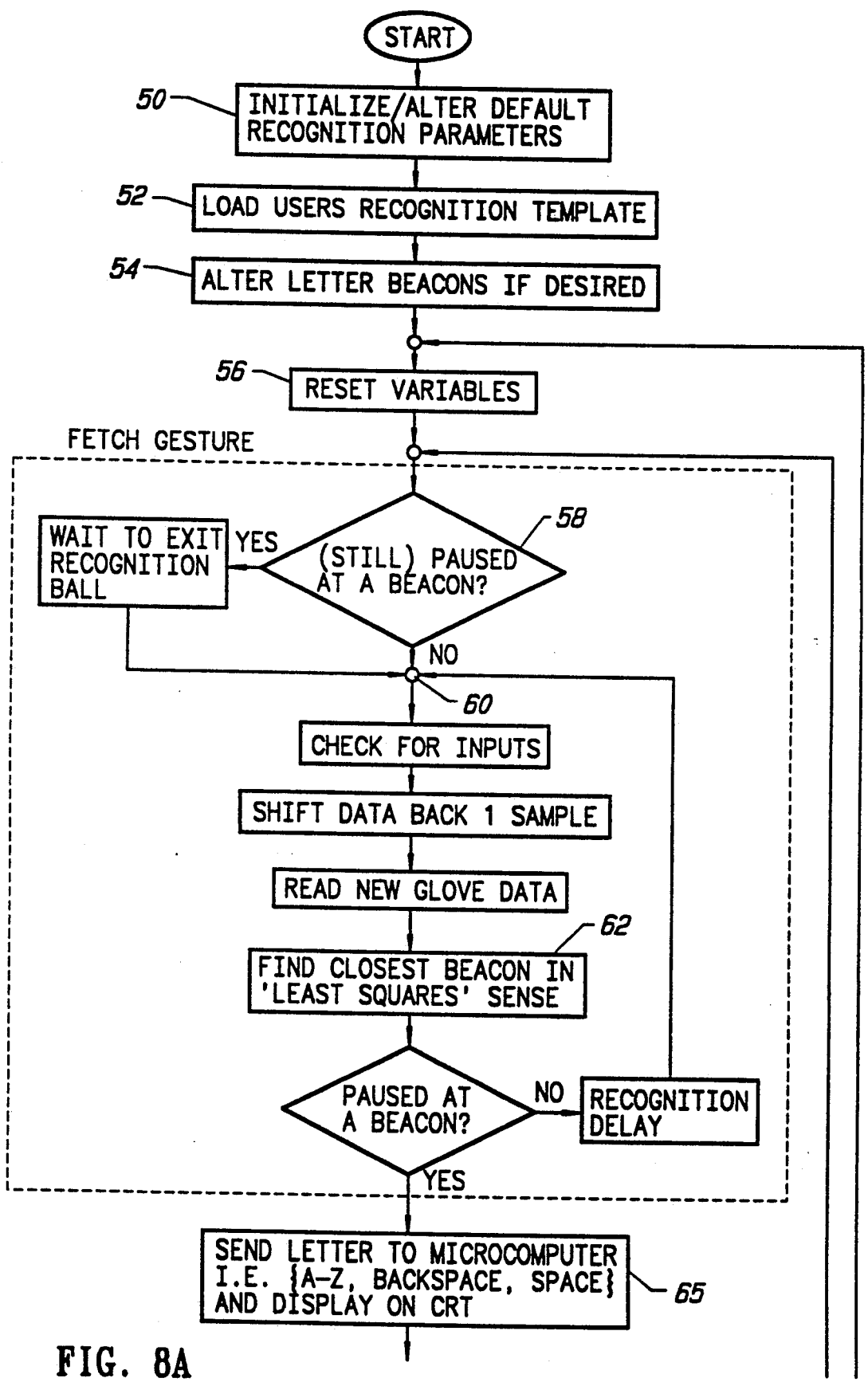
FIG. 8A and 8B are a flow diagram of software for implementing a letter recognition algorithm in the system of FIG. 7.
Figure 8B:
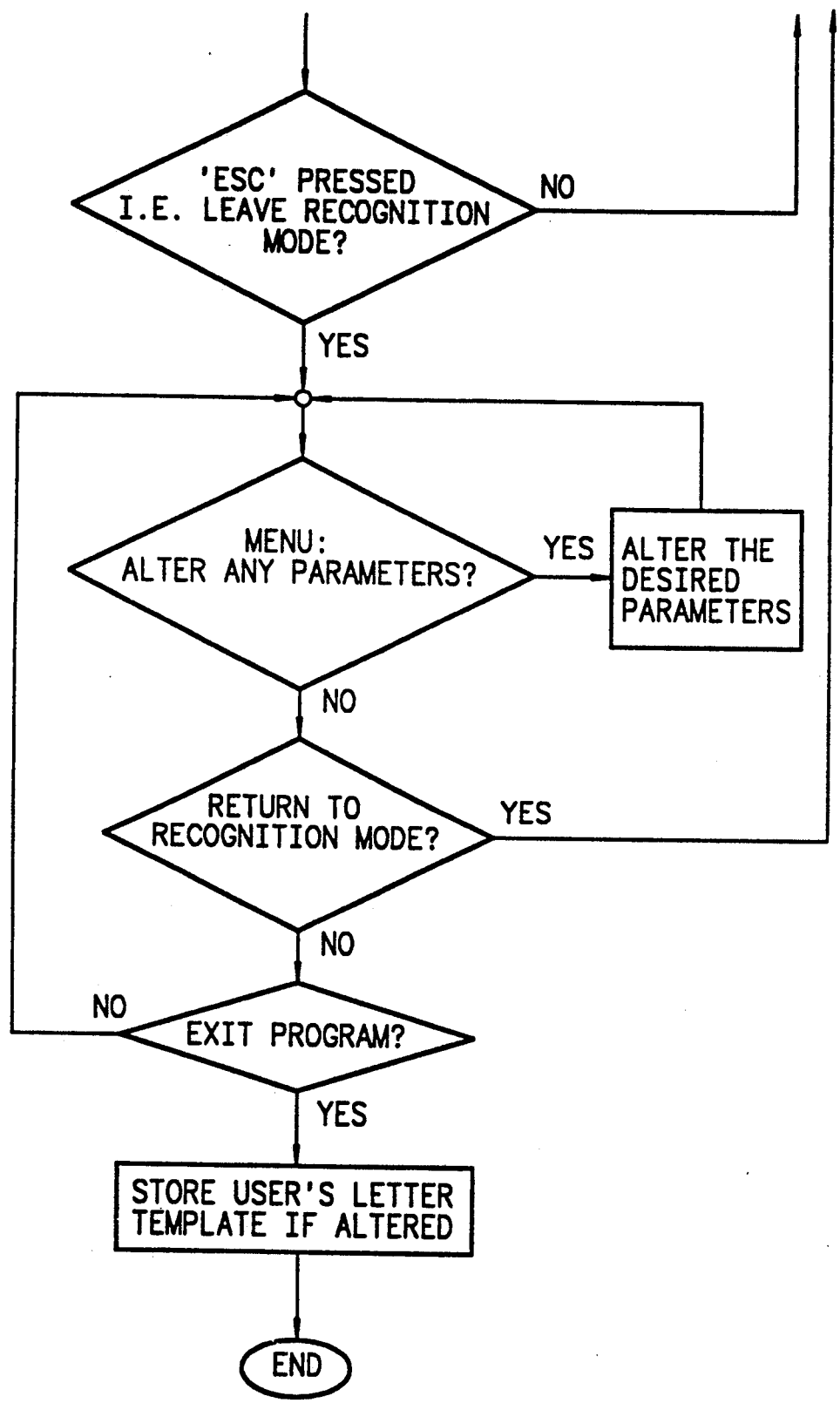

FIGS. 8A and 8B are a flow diagram of an earlier hand-pose recognition algorithm which was found to be satisfactory. The recognition algorithm was implemented in software, runs on the IBM AT computer and recognizes fingerspelled letters. Additional recognition algorithms, and modifications to the earlier recognition algorithm, which provide improved recognition performance are described later.

Figure 9:
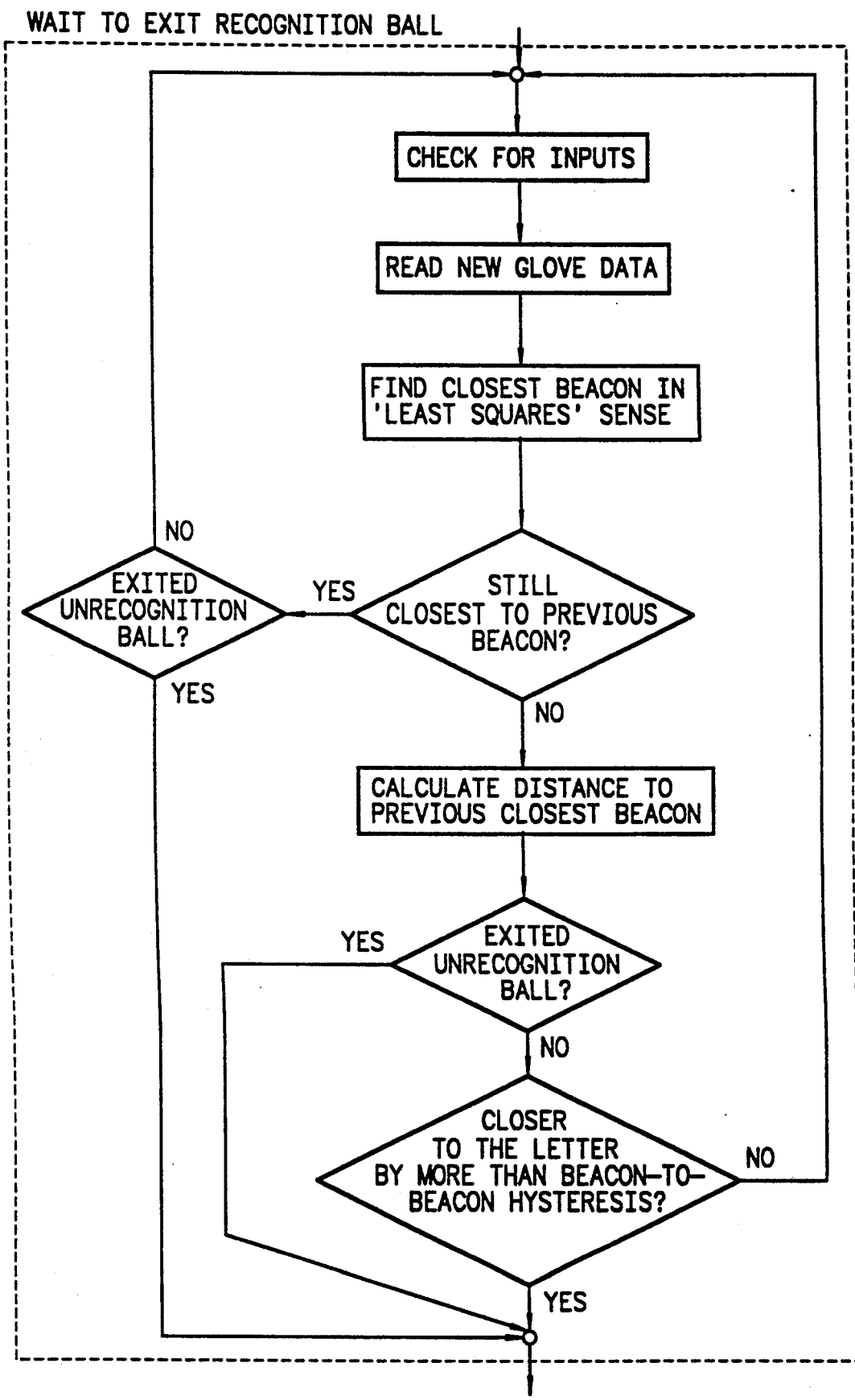
FIG. 9 is a flow diagram of a Wait to Exit recognition ball routine in the flow diagram of FIGS. 8A and 8B.
Figure 10:
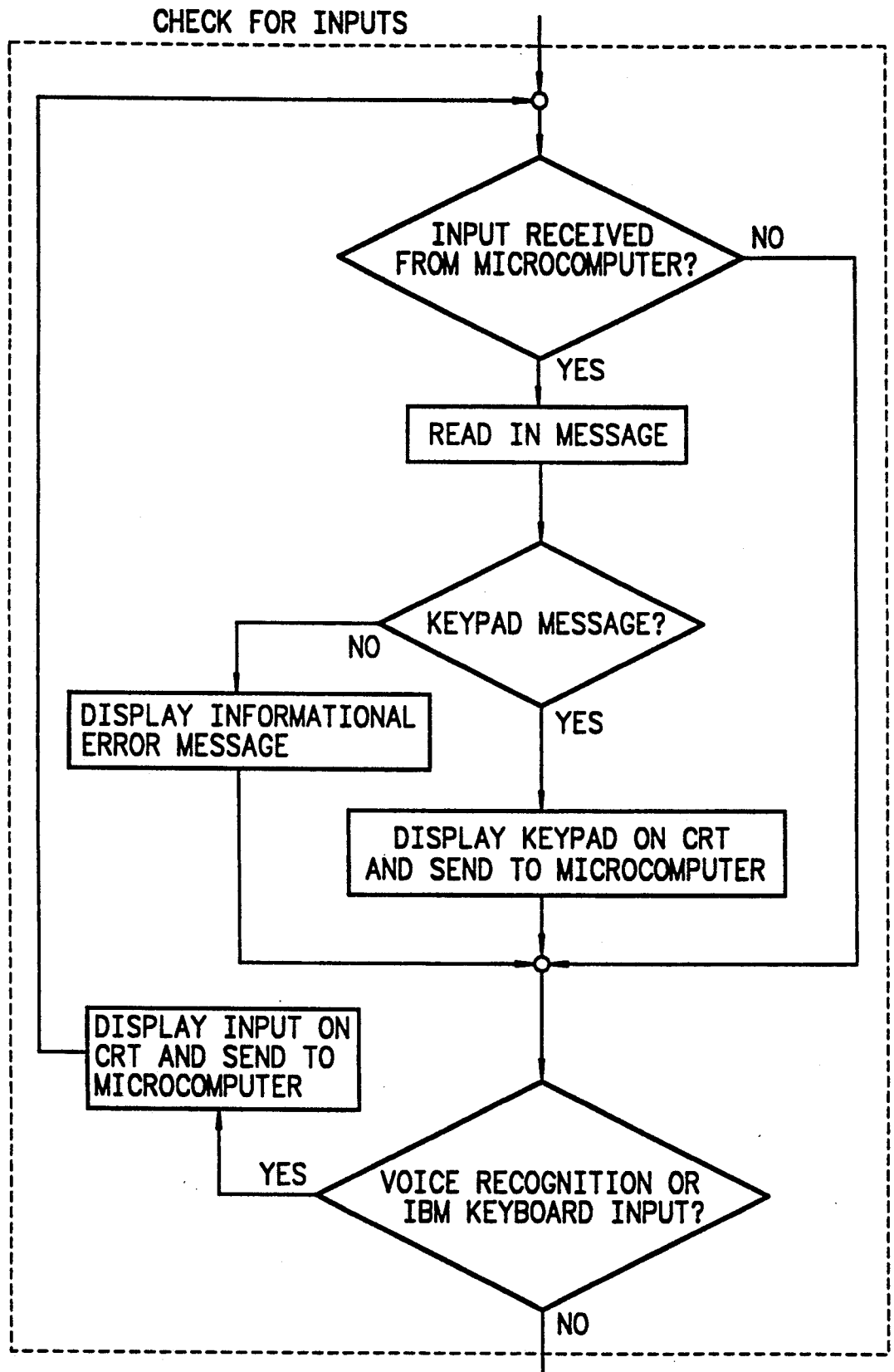
FIG. 10 is a flow diagram of a Check for Inputs routine in the flow diagram of FIGS. 8A and 8B.

FIG. 9 is a flow diagram of the Wait to Exit recognition ball routine and FIG. 10 is a flow diagram of the Check for Inputs routine as used in the letter recognition algorithm of FIGS. 8A and 8B. FIG. 11 is a flow diagram of the I/O and sampling software running on the Motorola microcomputer.

A printout of the software illustrated in FIGS. 8A, 8B, 9 and 10, written in Turbo Pascal, is attached hereto and incorporated by reference. A printout of the software illustrated in FIG. 11, written in Forth, is also attached hereto and incorporated by reference.

Referring now to FIG. 8A, the flow diagram for the letter recognition algorithm software begins with the initialize/alter default recognition parameters at 50. These parameters include the following:

1. recognition/unrecognition ball radii
2. beacon-beacon hysteresis margin that permits unrecognition if "substantially closer" to a new beacon
3. recognition confidence margin, required to recognize one beacon over the next nearest neighbor
4. recognition sampling period
5. maximum velocity that can denote a pause
6. number of sample points required to abide by parameters (1), (3) and (5), supra
7. joint weighting
8. additional letter 'c' recognition pause—to prevent incorrect recognition
9. voice selection (e.g. male, female, child)
10. select Dexter (mechanical fingerspelling hand) on/off, (FIG. 16a)
11. user name selection.

Next, the user's hand formation template, to be used during recognition, is loaded at 52. If the user is new to the system, then a default template is loaded. The hand formation template can be altered at 54 if desired by the user forming each of the letters and symbols sequentially and recording the sensor data corresponding to each letter beacon location.

Next, all variables are reset at 56 and then the Fetch Gesture routine is activated.

Determination of a pause at a beacon is made at 58.

For the Pause at a Beacon routine at 58 in FIG., 8A to produce a True, the following three questions must answer true: (1) pause? (2) inside a recognition ball? and (3) closer to the closest beacon than to the second closest beacon by more than the recognition confidence margin?

If Paused, then the Wait to Exit recognition ball routine (FIG. 9) is activated. If not paused, then the Check for Inputs routine (FIG. 10) is implemented. Next, previous sensor data values are shifted back in time one sample period prior to reading current sensor data to be used to recognize a new beacon for readout and storage. New glove data is read and the closest beacon is then determined using a "Least Squares" (L.S.) mathematical determination in 62. The Find Closest Beacon routine 62, has been optimized to very quickly search through all the possible beacons and record the closest and second-closest beacons. The quick search is achieved by first calculating the least squares distance to the previous closest and second-closest beacons. The remaining letter beacon distance are calculated in order of decreasing probability as determined from letter probabilities of the English language. Since the least squares method involves summing up the squares at the deviations of the selected beacon's joint sensor value, the calculation is checked after each squared deviation is added to the running total. If the intermediate sum is already greater than the previous second-closest beacon, the L.S. distance calculation for that beacon is terminated and the next beacon's distance determination is begun. In many cases, the previous closest and second-closest beacons will again be the new closest and second-closest beacons, so after the L.S. distances to these previous closest beacons has been calculated, only the first term in the L.S sum of the remaining beacon distances will need to be calculated. If the new closest beacons are not the previous closest beacons, the search algorithm calculates the beacon distances in order of decreasing probability so that as many of the following distance calculations as possible can be terminated prematurely. Thus computation time is dramatically reduced.

If it is determined from the new glove data that the user has not paused at a beacon, then a recognition delay is performed and new glove data is again read using the cycle described above. If it is determined from the new glove data that the user has paused at a beacon, then the letter corresponding to the beacon is displayed on the IBM monitor and then sent to the microcomputer for processing and display on the various peripheral devices shown in FIG. 7. Thereafter, the flow diagram proceeds to FIG. 8B where an escape variable is tested. If the escape variable tests positive, then the recognition loop is exited. Thereafter, the user can choose to alter recognition parameters, return to the recognition loop or exit the program. If it is desired to exit the program, the user's letter beacon template is stored to hard disk to be retrieved later at 52 when the program is restarted.

FIG. 9 is a flow diagram for the Wait to Exit recognition ball routine. After checking for inputs and reading the new glove data to determine a new hand-state position, the closest beacon is determined by using the numerical method of Least Squares. If the new hand state is still "closest" to the previously recognized beacon, then it is determined whether the unrecognition ball of the previous beacon has been exited. If not exited, the Wait to Exit recognition ball routine is started again. If it is determined that the unrecognition ball of the previous beacon has been exited, the Wait to Exit recognition ball routine is exited, returning control to the main program at 60 (FIG. 8A). If the new hand state is not closest to the previous beacon, then a calculation is made of the distance to the previous closest beacon. If the new hand state has exited the previous beacon's unrecognition ball then the Wait to Exit recognition ball routine is exited and a new beacon can be recognized. However, if the new hand state has not exited the unrecognition ball of the previous beacon, then it is determined whether the new hand state is closer to a new letter beacon by more than the beacon-to-beacon hysteresis margin. If yes, the Wait to Exit recognition ball routine is exited. If no, the Wait to Exit routine is repeated.

FIG. 10 is a flow diagram of the Check for Inputs routine. Basically the routine is looking for an input received from the microprocessor, a keypad message, voice recognition system or IBM keyboard input. If such messages are present, then they are displayed.

FIG. 11 is a flow diagram of the peripheral control and sensor sampling routine running on the Motorola microcomputer. Basically, the routine communicates with the IBM computer and controls the operation of peripheral devices shown in FIG. 7.

Although the recognition algorithms and related ideas provided below are described specifically in the context of recognizing finger-gestures the concepts are general and may be used in various applications including applications where it is desired to recognize a vector of features that are continuously varying in time. The newly developed treestructured neural net classifier, provided as a classification option in the recognition algorithm, may be used in many general classification applications requiring quicker training and classification than standard feedforward artificial neural networks.

In finger-gesture (hand-pose) recognition mode each sensor value is treated as one component of an overall "hand-state vector," i.e. each joint angle represents one axis in an n-dimensional "hand-space" where n is the number of sensors, e.g. instrumented joints. The number of sensors is typically at least about 14, preferably at least about 16, and may be 24 or more. As the fingers move, the hand-state vector traces a trajectory through hand-space, shown for a 3-dimensional space in FIG. 6. Initially, a training set is created where sensor information is stored for each hand-pose to inform the system of the user's finger-gesture statistics, i.e., "signature." Representative points, e.g., hand-pose mean values, for the training set of stored sensor values are represented figuratively by "beacons" in hand-space (FIGS. 6, 36).

Figure 37:
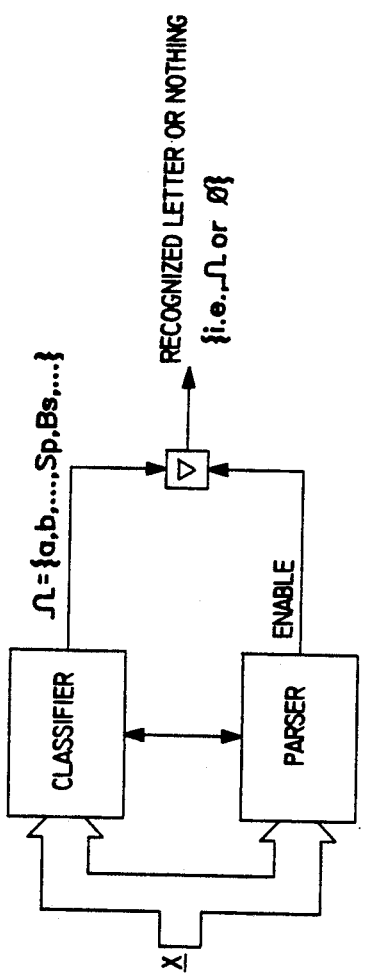
FIG. 37 is a block diagram showing a gesture parsing routine and classification routine which are part of an overall recognition algorithm.

The overall recognition algorithm includes a gesture parsing routine and a classification routine (FIG. 37) which work together to extract the desired hand-pose from continuously varying finger and wrist motion. When the parsing routine, which monitors the joint dynamics, detects a hand-state velocity minimum point (FIG. 30), one of various classification algorithms is used to determine the "nearest" predefined hand-pose (beacon) corresponding to the hand-state sample. The subject invention includes an option to select either a statistics-based classifier, or one of two artificial neural network classifiers. If the selected classifier determines that the instantaneous hand-state lies "close enough" to a predefined hand formation (where closeness is measured by some appropriate distance metric) the corresponding hand-pose is recognized. To avoid unintentional repeated recognition of the same hand formation, hysteresis 360 is introduced into the finger-gesture recognition algorithm by requiring that either the hand-state vector get "far enough" away from the recognized hand formation or the hand-state velocity to appreciably increase, before a new hand-pose is determined. At select times (for example after a fingerspelled word is spoken), the hand-pose beacons may be adaptively updated to reflect their new, most probable positions in hand-space. Continual adaptation reduces sensitivity to ongoing variations in hand-pose formation and sensor placement.

A simple adaptation scheme is a filter which only uses the most recent n samples of a letter to determine the hand-pose beacon mean and other statistics. So, when a hand-pose is recognized, the sensor data from the hand-pose recognized n samples ago is replaced with the new sensor data.

When the recognition algorithm is used in the communication system as previously described, the recognized hand-poses represent letters of the fingerspelling alphabet. When a hand-pose is recognized its corresponding letter label is placed in a word-assembly buffer. Backspacing is permitted and a "say it" hand-pose (i.e., beacon) also exists. If a backspace hand-pose is recognized, the erroneous hand-pose is not adapted. Once the "say it" hand formation has been recognized, the entire word in the word-assembly buffer may be output as synthesized speech to the hearing person preferably via a small speaker worn by the deaf individual (FIGS. 1, 2, 34A-34C).

As provided above, the subject invention includes an option to select either a statistics-based classifier, or one of two artificial neural network classifiers. The selected classifier utilizes the stored training (hand-state) vectors to classify a sample vector taken at recognition time. When the statistical classifier is used, each sensor value is modeled as a normally distributed random variable with mean equal to the centroid of the hand-pose samples, and thus, the hand-state vector is actually a multivariate normal random vector. The multivariate normal model has been verified by the inventors though Q—Q plots and statistical hypothesis testing. The statistical classifier is based on Bayesian Decision Theory which uses a priori probabilities about each hand-pose as well as a posteriori probabilities to select the hand-pose that is least probable to be in error. The a posteriori probabilities for each hand-pose are calculated for a given sample vector using knowledge of the probability density function (pdf) obtained from the stored training set.

Using the statistical (Bayesian) classifier and the assumption that the sensors values are random variables of a multivariate normal distribution, we define the square of a generalized distance measure, $d_1$, to be $$d_i^2 = r_i^2 + ln|S_i| - 2 \cdot ln[P(\theta_i)], \text{ where}$$
$$r_i^2 = (x - m_i)'S_i^{-1}(x - m_i)$$

and is called the weighted sum squared error (WSSE) or squared Mahalanobis distance for hand-pose i, x is the random hand-state vector, $m_i$ is the vector-valued mean of the samples for hand-pose i, $S_i$ is the sample covariance matrix of the random hand-state vectors for hand-pose i and $P(\theta_i)$ is the a priori probability of hand-pose i being the next intended hand-pose. Note that the equation for $r_i^2$ produces a family of concentric isovalue hyperellipsoids in x for each hand-pose, one curve for each value of r. Similarly, the equation for the generalized distance squared (GDS), $d_i^2$ produces a family of isovalue hyperellipsoids for each hand-pose. FIG. 36 shows two concentric hyperellipsoids for each of two letter hand-poses. Therefore, the classification rule reduces to selecting the symbol corresponding to the family of hyperellipsoids in which the hand-state sample lies inside the hyperellipsoid of smallest isovalue. In FIG. 36, point $p_3$ is closer to "A." Mathematically, the classification rule requires calculation of the WSSE distance from the hand-state sample to the centroid (mean) of each hand-pose, adds two terms which may depend on i, and then selects the hand-pose which is "closest." The WSSE distance calculation is a quadratic form, which in case of the Bayesian classifier, uses the inverse of the sample covariance matrix, $S_i$, as a weighting matrix, W. As a result, the directions in hand-space, as determined by the eigenvalues and eigenvectors of $S_i$, that had the most variability during training are given the least weight during recognition. Note that for the special case where the weighting matrix for a given hand-pose is set to the identity matrix, I, then all random variable components for that hand-pose are considered to have the same variance. Thus, all component errors are weighted equally and the WSSE distance measure reduces to simply a sum squared error (SSE) distance measure, and the hyperellipsoids reduce to hyperspheres. (Note: The sum squared error (SSE) distance is sometimes referred to as the least square (LS) distance, although, more accurately, "least squares" is a procedure for calculating regression coefficients subject to the constraint that the sum of the squares of the regression errors is minimized.)

The generalized distance from the sample hand-state to the expected closest hand-pose is calculated first to reduce the expected number of terms that are necessary to be calculated in the generalized distance to any of the remaining hand-poses, before that particular remaining hand-pose can be eliminated as a "closest" candidate. For example, if the closest hand-pose were known ahead of time and the distance to it calculated first, then the distances to each of the other candidate hand-poses is further. Therefore, since the WSSE distance calculation of the quadratic form $y'Wy$ consists of a sum over i and j of terms $W_{ij}Y_iY_j$, the summation calculation is preferably stopped when the running sum exceeds a critical distance, for example the distance to the closest or second closest hand-pose, or some predefined maximum acceptable distance. To further increase the chances that the running distance sum will pass the critical distance and be terminated as soon as possible, the weight matrix is spectrally factored into a summation of n terms, i.e., $W = S^{-1} = \Sigma_i(1/\lambda_i)v_iv_i'$ for $i = 1$ to n (the number of sensors) where $\lambda_i$ is the $i^{th}$ eigenvalue and $v_i$ is the $i^{th}$ eigenvector, or principal axis in hand-space, of the sample covariance matrix. (Note: Since eigenvectors are also called the principal axes, this method of spectrally factoring into eigenvectors is also referred to as Principal Component Analysis.) Then the generalized distance calculation becomes $$d_i^2 = \Sigma_i(1/\lambda_i)(x^t v_i)^2 + k_{1i} + k_{2i},$$

where $k_{1i} = \ln|S_i|$, $k_{2i} = -2^*\ln[P(\theta_i)] = -2^*\ln[P(\theta_i)]$ and $i = 1$ to n. Note that without loss of generality, $m_i$ was set to zero in the equation above for clarity which simply means that we are measuring the distance to a hand-pose with the coordinate system placed at the center of the hyperellipsoids corresponding to that hand-pose. Since $x^t v_i$ is the projection of x onto $v_i$, we can see, in the two sensor example of FIG. 36 that $x^t S^{-1} x > c^2$, where c is our critical isovalue, just by examining the first term of the sum, i.e., $|\lambda_1^{-\frac{1}{2}} x^t v_1| > |c|$. By calculating the WLS distance in this spectrally factored form we have also eliminated the need to invert the matrix, S, that becomes ill-conditioned as one of its eigenvalues approaches zero (and thus $|S|$ goes to 0), implying that one of the directions in hand-space is not being used.

In addition to finding the hand-pose beacon which is closest to the sample hand-state when the parse routine denotes a pause, other criteria are preferably imposed to help the recognition routine perform more reliably. For example, once the distance to the closest beacon is calculated the distance is compared to a "recognition maximum" distance for that beacon. If the distance from the current hand-state to the closest beacon is greater than the beacon's recognition maximum distance then recognition is not permitted. This insures that the closest beacon is "close enough" to be considered. For the feedforward neural net classifier which uses sigmoidal output units and has outputs ranging from $-1$ to $+1$, the recognition threshold value usually ranges from $-0.3$ to 0.99 and depends on the application. For a fingerspelling application, the threshold value is preferably set to 0.2. Note that for the typical feedforward neural net classifier, a sigmoid output nearer to $+1$ denotes that the sample hand-state is nearer to the hand-pose centroid and so the threshold is actually a minimum value, below which no hand-pose is recognized.

For the statistical classifier the generalized distance to the closest beacon must lie inside a recognition hyperellipsoid 351 of predetermined isovalue (FIG. 36). Since individual sensor values are modeled as normally distributed random variables and since the WSSE distance squared to any beacon is the sum of squares of normal random variables, then the square of the WSSE distance measure has a Chi-Squared distribution. Therefore, it is preferred to specify the recognition hyperellipsoid such that if the hand-state sample is outside that hyperellipsoid then the probability of error in not recognizing the corresponding hand-pose is below a specified maximum, $\alpha$. Mathematically speaking, this is equivalent to
$$Pr\{d^2 < X_n^2(\alpha)\} = 1 - \alpha$$

where $X_n^2(\alpha)$ is the value for an Chi-Squared random variable with n degrees of freedom, and $\alpha$ is the specified maximum probability of error.

The recognition algorithm may require a certain level of confidence before selecting one of two fairly close beacons. For example, it is preferred that a recognition confidence margin be used such that, even if all other recognition requirements are satisfied, the closest beacon must still be closer than the second closest beacon to the sample hand-state by more than the recognition confidence margin.

Hysteresis 360 (i.e., a dead-band) may be added to the recognition algorithm by requiring the hand-state vector to travel further from the recognized beacon before the beacon can be recognized again (FIG. 36). For the neural net routine, this corresponds to requiring the sigmoidal output to decrease below an "unrecognition" threshold value (below the recognition threshold) before the same letter can be re-recognized. For the statistical routine, the unrecognition threshold becomes an "outer" hyperellipsoid 362 (FIG. 36) beyond which the hand-state must pass before re-entry into the recognition hyperellipsoid will re-recognize the hand-pose.

In some cases two beacons can be so close that one is actually inside the other's recognition region. What is more often the case is that the sample hand-state lies inside more that one recognition region at the same time (e.g., $p_3$, FIG. 36). The problem that results is that the sample hand-state may be much closer to one beacon, but because a different beacon was recognized first, and the hand-state still hasn't left its unrecognition region, the closer beacon isn't recognized. To remedy this situation, an unrecognition confidence margin is set such that if the hand-state is closer to a new beacon than the currently recognized beacon by more than the unrecognition confidence margin, then the currently recognized beacon is unrecognized and the new beacon is recognized.

Figure 39A:
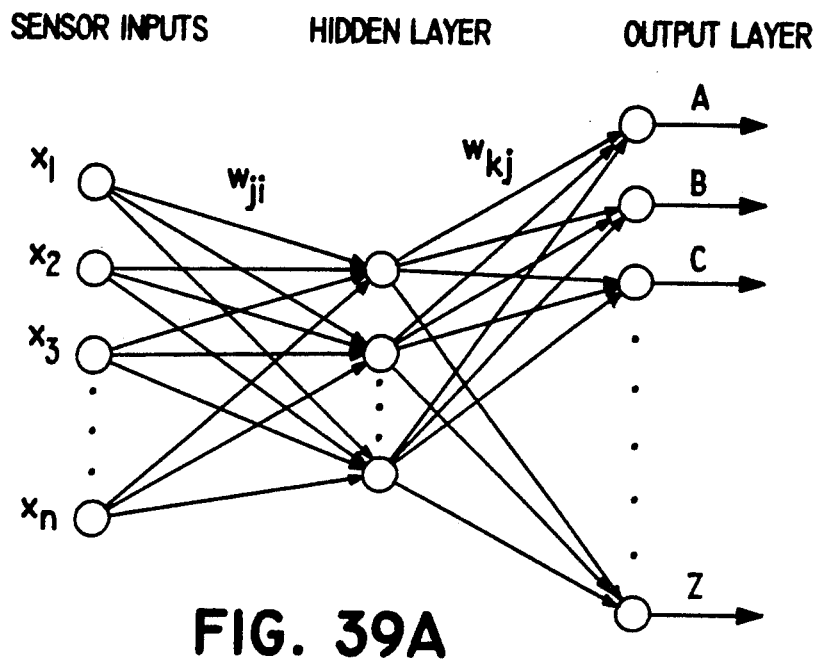
FIG. 39A is a feedforward neural network.
Figure 39B:
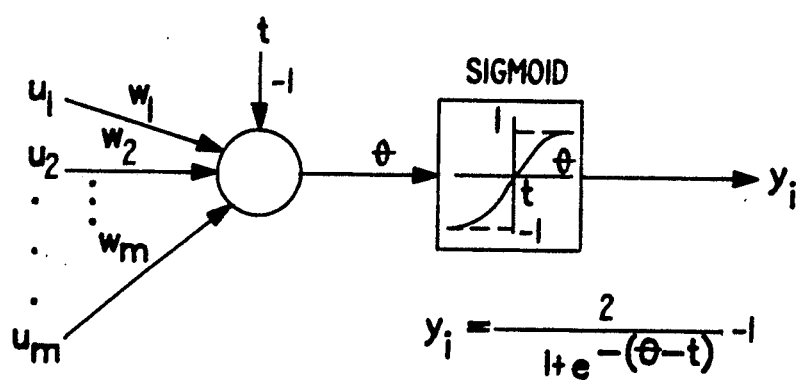
FIG. 39B is a sigmoidal squashing function.

As mentioned above an artificial neural network structure may be used to classify sample hand-states. The subject invention provides two possible neural net structure which may be used to train hand-poses and recognize sample hand-states. The first is a feedforward neural net as shown in FIG. 39A. At the far left are the input nodes. There is preferable at least one input node per sensor. In the simplest case there is one input node for each sensor value. In more complicated cases there may be position, velocity, acceleration, position squared and the like, inputs for each position sensor. Input values are scaled to occur in the range of $-1$ to $+1$. Each input value is connected to one or more of the nodes in the middle layer. The nodes in this layer are called hidden units. Each unit sums its weighted inputs (including a weighted constant input, called the bias) and then passes the sum though a sigmoidal squashing function (FIG. 39B) that produces an output between $-1$ and $+1$. Each of the outputs of the hidden units may be used as input to additional hidden layers or may be input to one or more units of the output layer. As with the hidden units, the output units sum weighted outputs from the previous layer and then pass the sum though an additional function which may be sigmoidal, linear or other appropriate function.

There are various ways to train the network to classify hand-state vectors. The prefered training method is to assign each hand-pose to be recognized to a different output unit. When training the net to recognize a vector known to come from class i, a desired output vector consisting of $-1$ at the output of all output units except an output of $+1$ at unit assigned to class i, is used. The Backpropagation (Sigmoid LMS) learning algorithm is conveniently used to train the weights interconnecting the various layers of units to produce an output vector which is close to the desired output vector for each input vector in the training set. Learning rates usually in the range of 0.001 to 0.5 are used, whereas a rate of 0.1 is preferably used to train hand-poses corresponding to letters of the fingerspelling alphabet. Techniques such as momentum, simulated annealing and the like may be used to enhance the learning algorithm.

When the training method described above is used along with appropriate offset, scaling and normalization to produce outputs in the range from 0 to +1 with all outputs summing to 1.0, the output value from a particular unit in the output layer is representative of the probability that the input sample hand-state should be assigned to the class corresponding to that output unit. When classifying a sample hand-state input vector, the class corresponding to the output unit with the largest output, i.e., highest probability, is selected as "closest." However, as explained above, when the recognition algorithm of the subject invention is used, other criteria may also be required before the closest beacon will be recognized.

Figure 40A:
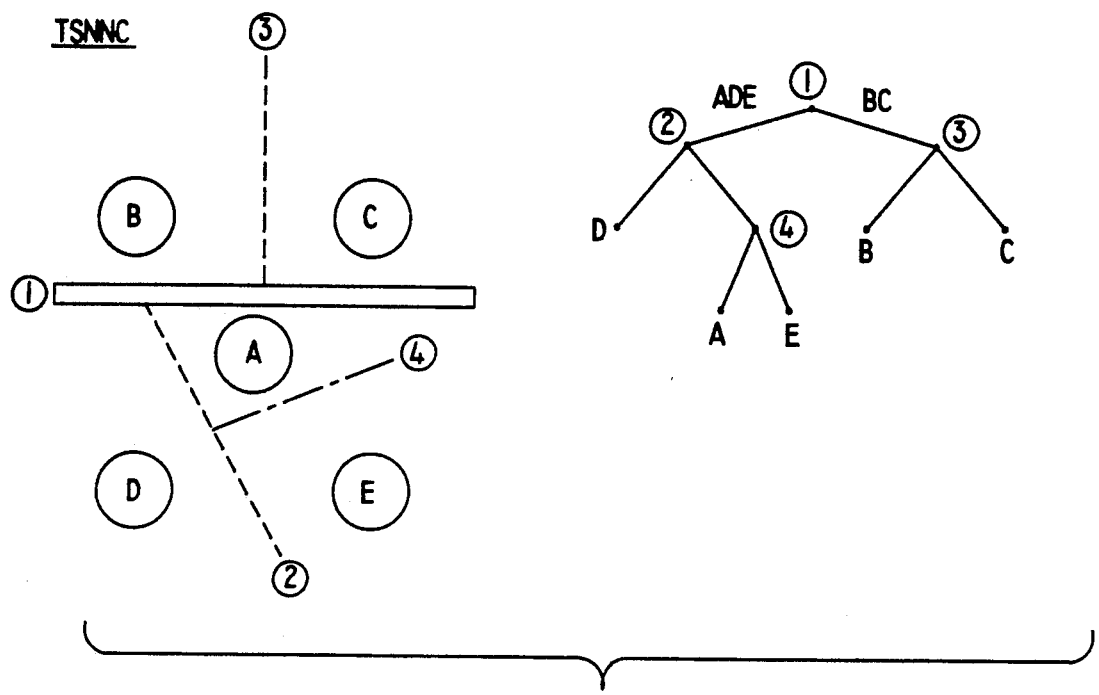
FIGS. 40A and 40B are two example sets of clusters of labeled training data points and corresponding TSNNC decision trees.
Figure 40B:
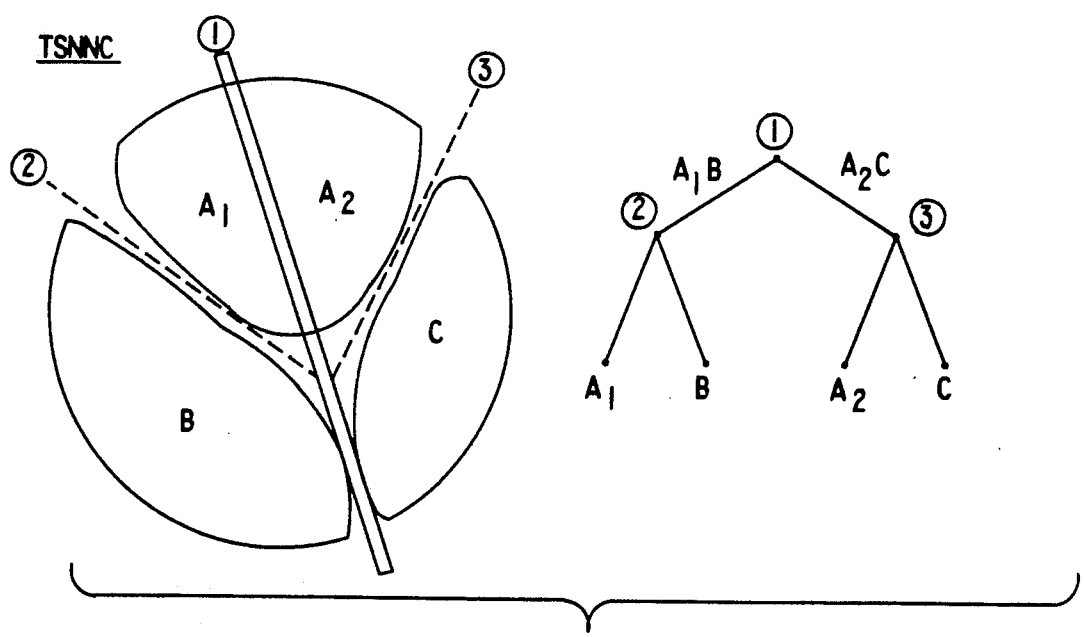

The subject invention also provides a newly developed neural network algorithm that may be used to perform general classification tasks, and specifically, to classify hand-poses. The algorithm is a treestructured neural network classifier (TSNNC). During training of a labeled data set, a decision tree is constructed which is then used during the subsequent recognition phase to classify a sample input vector based on a number of decisions, one decision per node of the tree. FIGS. 40A and 40B show two example sets of clusters of labeled training data points and the corresponding possible resulting binary trees produced by the TSNNC. This TSNNC algorithm will always produce a zero-error solution on convex training sets. The maximum rate (i.e., length of the tree) is guaranteed to be less than the number of data clusters to be classified. Therefore, the number of multiply/adds less than a simple feedforward neural net with the same number of inputs, output units and with no hidden units.

Figure 41A:
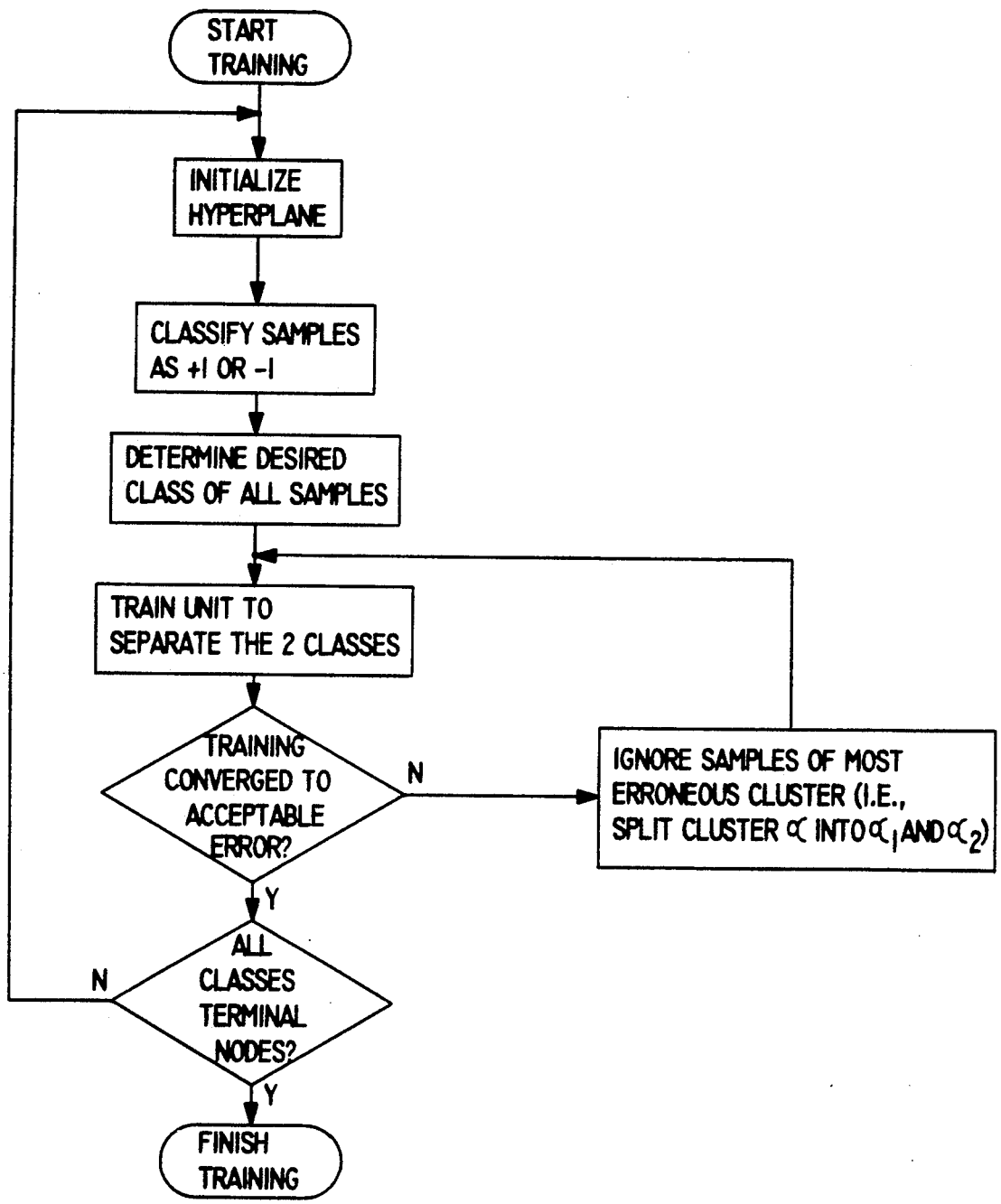
FIGS. 41A and 41B are block diagrams of the TSNNC training and classification algorithms respectively.
Figure 41B:
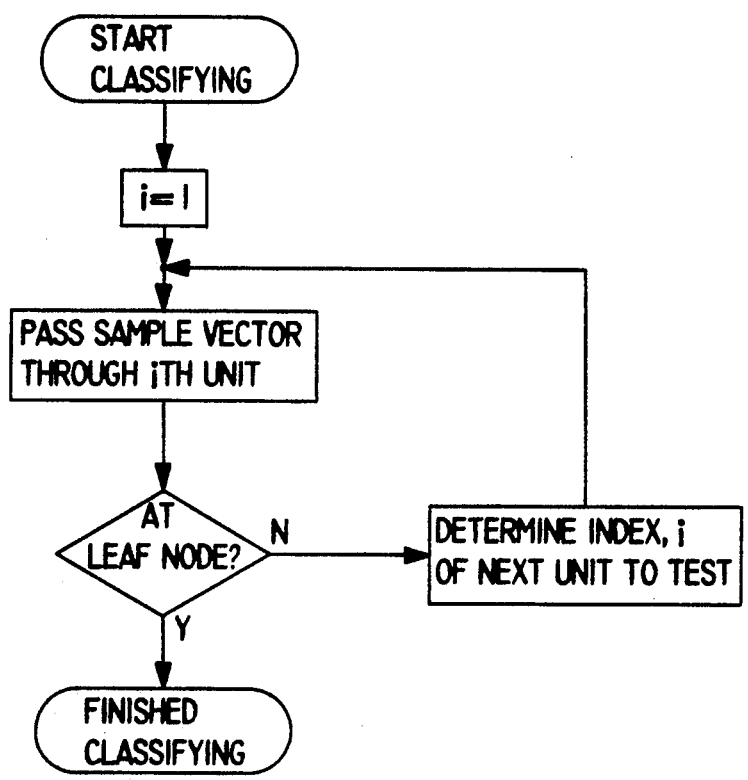

FIG. 41 provides a flow diagram of the TSNNC algorithm for constructing a binary decision tree. The first step to construct the decision tree for a given labeled data set is to initialize a hyperplane to pass though the centroid of all the samples. Note that a single sigmoidal unit (FIG. 39b) is a function which passes the sum of its weighted inputs through a sigmoidal squashing function and returns a real valued result between $-1$ and $+1$. When the equation for the sum of the weighted inputs is plotted in weight-space, i.e., each axis represents the value of one of the d input weights, the resulting curve is called a d-dimensional hyperplane. The hyperplane is initialized parallel to the eigenvector corresponding to the minimum eigenvalue of the scatter matrix of the points to be separated. Next, using a single sigmoidal unit, all data points are classified to belong to either the newly created $-1$ class or the $+1$ class. By belonging to the $-1$ class, it is meant that the desired sigmoidal unit output value of all points assigned to the $-1$ class is $-1$. Similarly, the desired unit output value of all points assigned to the $+1$ class is $+1$.

The individual data sample classification error is defined to be the difference between the desired sigmoidal unit output value (as determined by the assigned class label of either $-1$ or $+1$) and the actual unit output. For each original cluster of labeled data, the sum squared error (SSE) is calculated that would result if all the samples in that cluster that were assigned to the newly created $-1$ class were to be assigned to the $+1$ class. Similarly, the SSE is calculated that would result if all the samples in the cluster in question that were assigned to the newly created $+1$ class were assigned to the $-1$ class. For each original cluster, the value which would induce the least SSE is chosen as the desired class value (i.e., $-1$ or $+1$) for all the samples of the cluster.

Using an appropriate learning algorithm, such as Backpropagation (Sigmoid LMS), the unit is trained to separate all the clusters into the two classes. Simulated annealing may be used to help prevent the solution from getting stuck in a local minimum. The intuition behind the relabeling and training is to attempt to get all data points in a single cluster on the same side of the dividing hyperplane, and to choose a class value for each cluster such that the hyperplane is required to move the least.

If after training a unit, the final mean squared error (MSE) over the sample points of all clusters divided by that unit is "small enough," and all clusters are at a leaf node of the tree (i.e., there is only one cluster assigned to the $-1$ class and one to the $+1$ class for a particular unit), stop, the training algorithm is finished and a decision tree has been constructed. If the final mean squared error (MSE) from training a unit is "small enough," but not all clusters are at a leaf node of the tree, then that unit is considered "fully trained" and a new unit (hyperplane) is initialized, similar to above, which further divides all the samples of the clusters assigned to that class. Now proceed in the same manner as was done previously where all sample points of a particular cluster are assigned to a class such that the induced SSE is minimized. The newly added unit is then trained until it converges to an acceptable MSE. If again, all clusters are not leaf nodes, a new unit (hyperplane) is initialized and trained. In other words, to continue, the samples assigned to a single $-1$ or $+1$ class are further subdivided with more hyperplanes until the last hyperplane divides only two clusters, which are at leaf nodes of the tree.

The procedure just described works fine for designing a tree to classify clusters that are linearly separable at each branch. However, when the clusters at a branch are not linearly separable the learning algorithm will not converge to a sufficiently small MSE. If the clusters to be separated by a unit are not linearly separable but are convex, the following modification is made to the algorithm. The cluster, call it $a$, that is contributing most to the total MSE is selected, all its samples are ignored and the unit is further trained on the samples from the remaining clusters. If the training converges this time, that unit is considered fully trained. However, with this unit, cluster $a$ has just been divided into two pieces, $a_1$ and $a_2$, where $a_1$ is a sub-cluster assigned to the $-1$ class and $a_2$ is a sub-cluster assigned to the $+1$ class. The TSNNC algorithm continues from this point as if it has just divided the clusters without splitting a cluster into two. If after removing the samples from cluster $a$, the training routine still does not converge, the procedure of finding the cluster which now contributes most to the MSE is repeated, all its samples are ignored and training is continued. The process of ignoring clusters of samples will occur at most m $-2$ times per unit before the training for that unit will converge, as long as the clusters are convex, and where m is the number of clusters to be separated by that unit. In the worst possible case where each unit must ignore m $-2$ clusters, or where the unit is otherwise able to separate only one cluster from the m $-1$ remaining clusters at a time, leaving m $-1$ clusters to be separated by the next unit, the maximum length tree of length m $-1$ is constructed. This means that it will require m −1 binary decisions to classify an arbitrary sample vector.

The recognition process for the constructed decision tree is very quick and simple. Whereas sigmoidal units were required by the learning algorithms suggested, simple binary signum units are used during recognition. That is, at each branch in the tree, the inputs are weighted by the weights as determined in the training procedure, summed and the sum simply compared to zero. If the sum is greater than zero one child branch is followed, if the sum is less than zero the other child branch is followed. Once a leaf node is reached the sample input test vector is classified as belonging to the same class as the cluster trained to correspond to that node.

The main drawback of the TSNNC algorithm is that it is harder to tell how "close" the test vector was to the centroid of any cluster so such ideas as (un)recognition thresholds and (un)recognition confidence margins and the like may be harder to employ. One solution to this problem is to simply use the TSNNC to quickly determine the closest beacon and then go back and calculate the generalized distance or neural net distance from the test vector to that same beacon, and use that distance when comparing to (un)recognition thresholds, etc.

Figure 38:
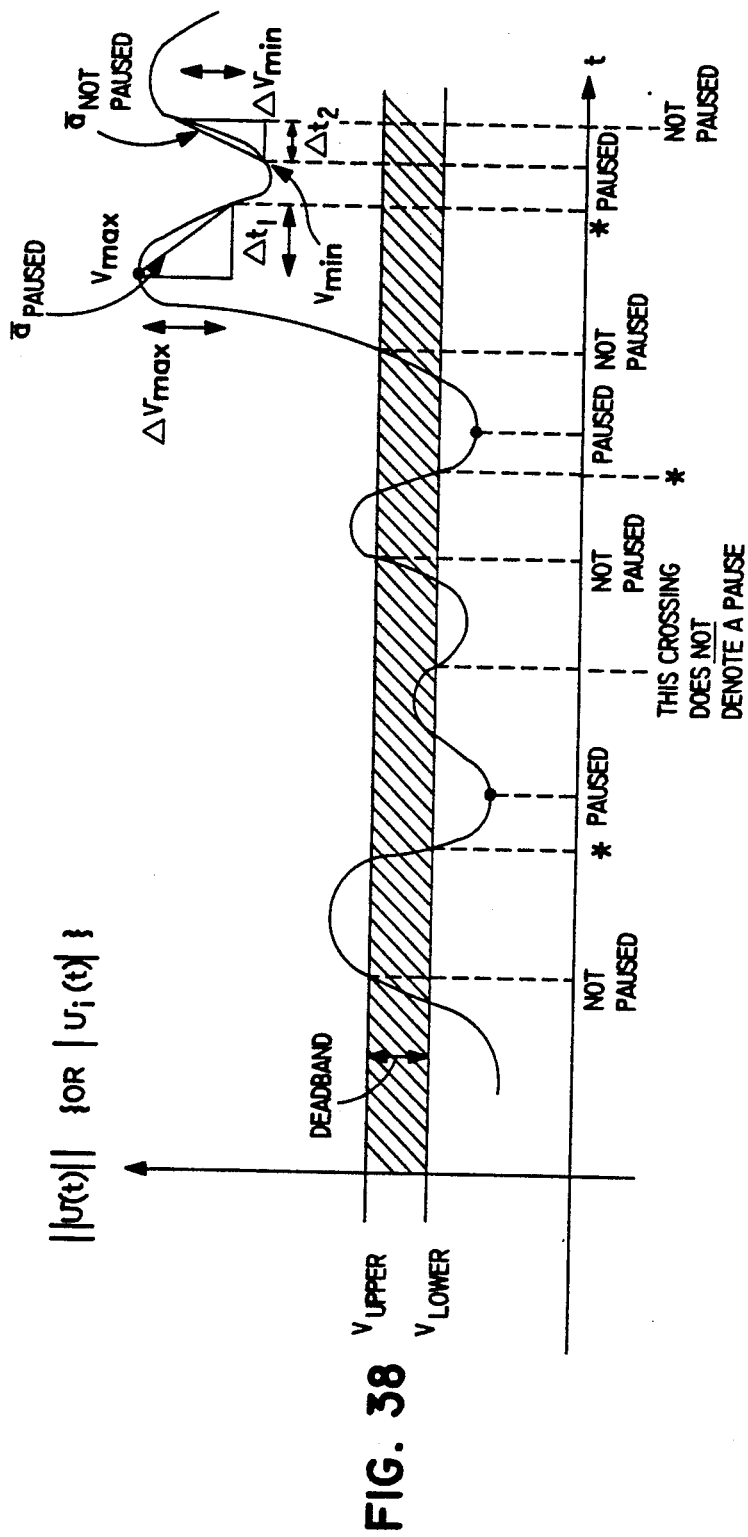
FIG. 38 is a plot of an example hand-state velocity vector magnitude versus time curve with various points of interest marked.
Figure 42:
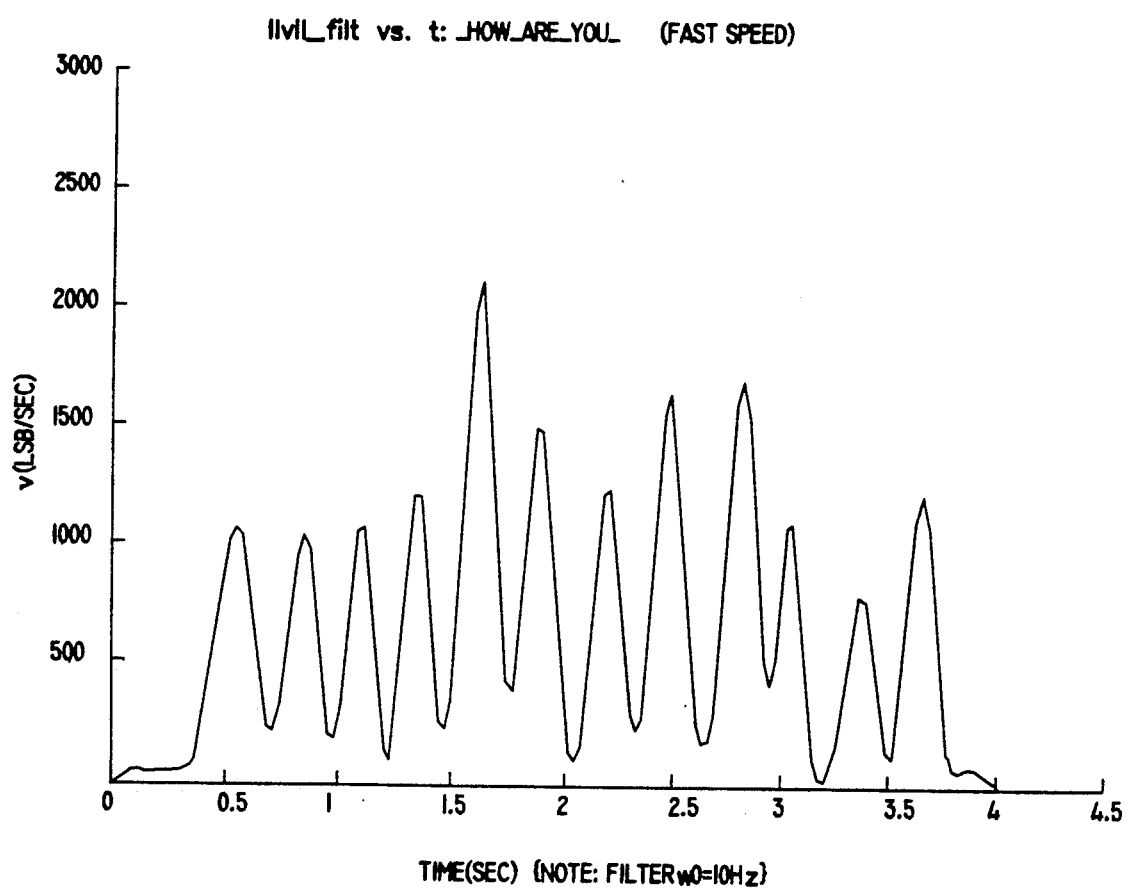
FIG. 42 is a plot of an example hand-state velocity vector magnitude versus time.

As previously mentioned, a gesture parsing routine works closely with the chosen classification routine to select the desired hand-pose at the appropriate time. The parsing routine calls on several other routines and functions to help it make a parsing decision. For example, the parsing routine communicates with a pause detector which, among other duties, determines when the hand-state velocity reaches a minimum point (FIGS. 38, 42). The parsing routine also takes the distances from the hand-state vector to the various closest hand-poses and compares these distances to the (un)-recognition thresholds and (un)recognition confidence margins.

To better understand the pause detection routine, refer to FIG. 38 which shows an example hand-state velocity vector magnitude (i.e, $||v||$) versus time curve with various points of interest marked. As is seen, not all points at a velocity minimum are considered "pause points." There are several requirements for a velocity minimum to be considered a pause point. The first requirement is that prior to the velocity minimum the hand-state must have been considered "not paused." This requirement reduces the probability that a hand-pose will be incorrectly re-recognized. If the hand-state is not considered to be paused $V_{lower}$ and the hand-state velocity dips below a lower velocity threshold ($V_{lower}$) and reaches a minimum, the hand-state is considered paused. If the hand-state is not paused and the hand-state velocity is not below $v_{lower}$, there are two ways for a pause to be detected. A pause will be declared at a velocity minimum point which occurs after the velocity has been determined to fall a predefined percentage below the maximum velocity ($V_{max}$) achieved since the hand-state was determined not to be paused. Mathematically, this is saying that there exists a velocity pause threshold, $T_{vp}$, (which may depend on $V_{max}$) such that if $(\Delta V_{max}/V_{max}) < T_{vp} < T_{vp} < 0$ then a pause will be declared at the next velocity minimum. Note that the quantities are all less than zero since velocity is decreasing and thus $\Delta V_{max}$ is negative. A pause will also be declared at the first velocity minimum if, once a set amount of time has passed since a velocity maximum, the average deceleration is greater than a preset amount. This is equivalent to saying that there exists an acceleration pause threshold, $T_{ap}$, (which may depend on $v_{max}$) such that if $(\Delta v_{max}/\Delta t_1) < T_{ap} < 0$ (where $\Delta t_1$ is $>=\Delta t_{1min}$) then a pause will be declared at the next velocity minimum. In summary, among other criteria for a parse to be determined and the closest hand-pose to be recognized, the hand-state must be paused, the hand-state must be "close enough" to the closest hand-pose, the hand-state must be sufficiently closer to the closest hand-pose than the second closest hand-pose, and the no hand-pose may be currently recognized.

Once the hand-state is considered paused, there are several ways for it to be "unpaused." If the hand-state was declared paused at a velocity minimum that was below $V_{lower}$, then the hand-state is declared unpaused when the velocity surpasses an upper velocity threshold, $V_{upper}$. If the hand-state was declared paused at a value above $V_{lower}$ then it may be declared unpaused whenever either of two criterion are met. One way for the hand-state to be declared unpaused is if the velocity rises a predefined percentage above the velocity minimum point. This is equivalent to saying that there exists a velocity unpause threshold, $T_{vu}$, (which may depend on $V_{min}$) such that if $(\Delta v_{min}/v_{min}) > T_{vu} > 0$ the hand-state is declared unpaused. The hand-state is also declared unpaused if, once a set amount of time has passed since the velocity minimum, the average acceleration is greater than a preset amount. This is equivalent to saying that there exists an acceleration unpause threshold, $T_{au}$(which may depend on $V_{min}$) such that if $(\Delta v_{min}/\Delta t_2) > T_{au} > 0$ (where $\Delta t_2 > =\Delta t_{2min}$) then the hand-state is declared unpaused. In summary, among other criteria, a hand-pose is considered unrecognized whenever the hand-state vector is declared unpaused, or it is "far enough" away from the recognized hand-pose or it is "close enough" to a new hand-pose.

Figure 43:
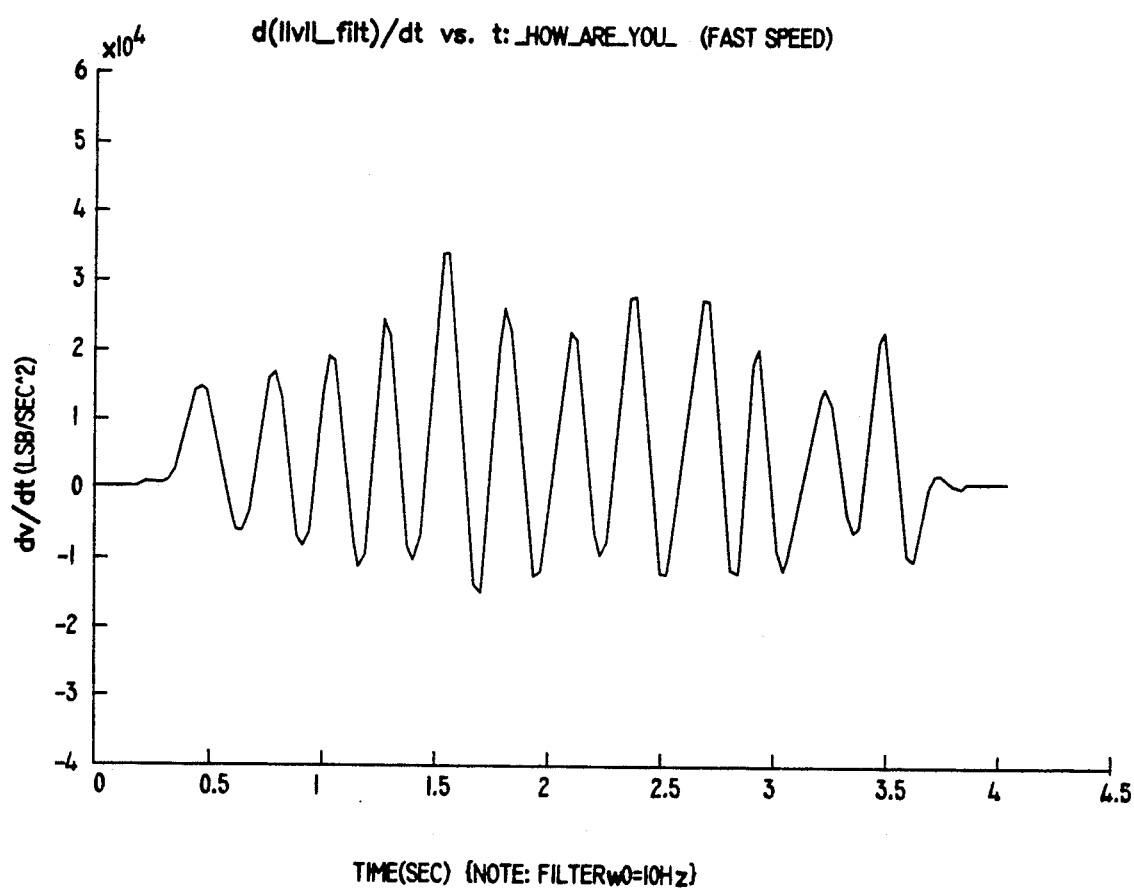
FIG. 43 is a plot of an example hand-state acceleration vector versus time.

To determine the point where the velocity reaches its minimum, the value of instantaneous acceleration (i.e., $d||v||/dt$) may be used (FIG. 43), since when the magnitude of velocity, $||v||$, is decreasing to a minimum, the value of the hand-state acceleration is increasing toward zero from a negative value. Therefore, by simply watching for when the acceleration reaches the acceleration threshold value just below zero, the velocity minimum point will be satifactorally determined. By having the acceleration threshold value just below zero, this technique has the added benefit that it will also detect when the velocity is slowly approaching a constant value.

Several vector norms may be used to convert the velocity and acceleration vectors to scalar values that can be compared to thresholds, etc. The preferred vector norm is the 2-norm (i.e., Euclidean norm), however other popular norms such as the 1-norm, infinity-norm or general p-norm may be used. To calculate the 2-norm of a vector, the components of the vector are squared, added and then the square root of the sum is taken. However, this calculation implies that motion from all sensors should have equal weighting. This is not necessarily a good idea. Take, for example, the case of finger-gesture recognition. Different sensors may be used which have different inherent gains built in, or similar sensors may be placed on different parts of the hand which move through different angular ranges. The signal from one sensor may be known to be of less importance than the signal from another, if so, weighting should reflect the relative importance.

When the statistical classifier is used, the norm for the velocity vector may use the same weights that are used by the classifier, i.e., $W=S_i^{-1}$. Mathematically, this is equivalent to $|v|_{2,W}=(v^T W v)^{\frac{1}{2}}$, where the subscript 2 means the 2-norm and the subscript W means weighted by matrix, W. By using the inverse of the sample covariance matrix to weight the hand-state velocity vector, those velocity components that correspond to directions in hand-space that had a lot of variance during training of a particular hand-pose will not receive a lot of weight when attempting to detect a pause. The same weight matrix, i.e., $W=S_i^{-1}$, may also be used to weight the hand-state velocity vector when one of the neural net classifiers is used. To use this weighting scheme for any of the classifiers, the closest hand-pose must first be determined so the appropriate weighting matrix may be selected. Therefore, for every hand-state sample the closest and second closest hand-poses and their corresponding distances are determined. If all other criteria for recognition pass, e.g., the closest hand-pose is close enough, and sufficiently closer than the second closest hand-pose, then the weighted velocity norm and the associated acceleration are calculated using the weighting matrix corresponding to the closest hand-pose, and it is determined if the hand-state is paused.

An alternate weighting scheme is to weight each velocity component by the gain necessary to expand the positional range of the corresponding sensor value to a chosen standard value. For example, if values from sensor one only ranged between 0 and 25, while values from sensor two ranged from 0 to 50, then if the standard value were chosen to be 100, the gain for sensor one would be four, while the gain for sensor two would be two. These same gains would be applied to the first two components, respectively, of the velocity vector norm calculation.

Figure 44:
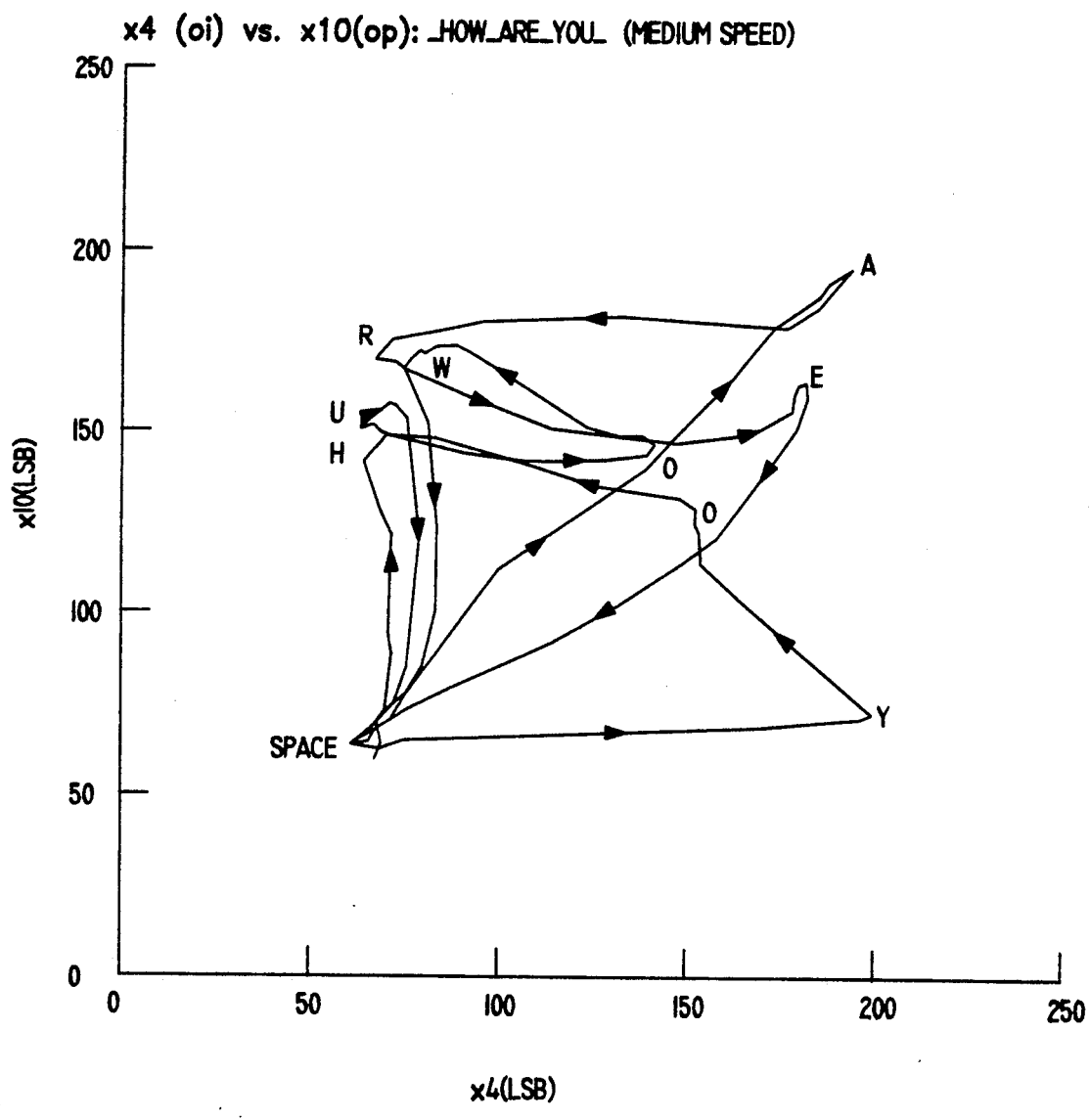
FIG. 44 is an example 2-D curve of hand-state trajectory.

The effectiveness that the pause detection routine has in helping to parse a continuously moving vector of values depends on how the coordination between the values changes near a vector of interest. In particular, the pause detection routine is very effective in aiding to extract fingerspelled letters from a continously moving hand-state vector due to some important observations about how the coordination of the fingers and hand vary near a desired letter. For example, during fingerspelling, between most letter hand-poses the fingers move in a coordinated manner, where the fingers begin moving at the same time, accelerate and decelerate together, and arrive at the final hand-pose at the same time. The few exceptions to this rule are handled on an individual basis. In the same sense, when one hand-pose is reached and the fingers start toward the next hand-pose, relative accelerations occur between joints which correspond to curvature of the hand-state trajectory (FIG. 44). These relative accelerations between the joints cause the norm of the hand-state velocity vector to unintentionally pass through a minimum at the letter hand-pose. Therefore, in most cases, a velocity minimum corresponds to a fingerspelled letter.

There are, however, exceptions to this rule that must be handled individually. For example, when fingerspelling "B-O-Y", no intentional pause need be added to the "O" for a pause to be detected since some previously moving joints stop while some non-moving joints begin moving when the "O" is reached. These changes in joint coordination produce a velocity minimum. However, if one were to spell, "B-C-O-Y", an intentional pause would be needed to recognize the "C" since it is "on the way" from a "B" to an "O" and so the joint coordination remains constant. This actually doesn't present a problem since most people who would fingerspell "B-C-O-Y" would also add a short pause to make it visually clear what the letter was, if it were not clear from context.

Another example is when fingerspelling "A-T" the norm of the hand-state velocity actually passes through a minimum, where there is no letter, on the way from "A" to "T". In this particular case the "extra" minimum is due to the fact that in going from "A" to "T" the index finger is lifted over the thumb. As the finger reaches its peak and starts coming down it passes through a zero velocity point which causes an overall hand-state velocity minimum. If the recognition thresholds are set to a "tight" value, no letter hand-pose will be close enough and so the pause detector won't even be invoked. If the recognition thresholds are set to a "loose" value, then a letter hand-pose may be close enough to be recognized, so when the velocity passes through the minimum, an erroneous letter will be recognized. To remedy this situation, a "transition letter" may be trained at the location of each velocity minimum point. These transition letters are hand-poses that never show up, i.e., they are never printed nor spoken, but are there as "recognition sinks" to prevent the erroneous recognition of a "real" letter. One possible tedious algorithm to train the transitions letters is to perform every letter-to-letter transition and let the training algorithm create a new transition letter whenever a velocity minimum is detected that does not occur "near" one of the trained letters or previously defined transition letters.

The instrumented glove and communication system in accordance with the invention offer distinct advantages over known prior-art communication systems. The instrumented glove utilizes linear sensors and is insensitive to bend radius and joint coupling. Importantly, the glove is easily and inexpensively manufactured. The use of annealed, high-elongation strain gages in extremely thin and flexible sensors ensures that maximum stress seen by the gages is below acceptable limits. The glove and communication system provide a fingerspelling-to-speech system heretofore unavailable. The system enables a nonvocal person to "talk" with several hearing or deaf individuals simultaneously. The adaptive letter recognition algorithm is reprogrammable using "soft" decisions. The several peripheral output devices enable communication with vocal, nonvocal, deaf and deaf-blind individuals.

While the invention has been described with reference to specific embodiments, the description is illustrative of the invention and is not to be construed as limiting the invention. For example, the instrumented glove can be used as an input device in other man-machine environments such as in the control of robotic devices, as a cursor controller, and in artificial limb control, for example. Additionally, the variable resistance strain sensing goniometer sensor in accordance with the invention can be used in other garments and support structures for use by humans, other animals, and even inanimate objects.

Various modifications and amplifications may occur to those skilled in the art without departing form the true spirit and scope of the invention as defined by the appended claims.

What is claimed is:

1. A goniometer capable of following an angle of bending to at least about 115 degrees, said goniometer comprising:
an inert thin electrically non-conductive flexible support backing,
first and second variable resistance strain sensing elements affixed on opposite sides of said backing; and
means for electrically connecting each of said elements.

2. A goniometer according to claim 1, wherein resistance of said sensing elements varies linearly with strain of said sensing elements.

3. A goniometer according to claim 1, wherein said backing is a single film.

4. A goniometer according to claim 1, wherein said backing is two films adhered together.

5. A goniometer according to claim 1 in a fixed U-shape.

6. A goniometer according to claim 5, further comprising means for preventing bending beyond the minimum bend radius.

7. A goniometer according to claim 1, wherein said first and second sensing elements are substantially overlapping.

8. A goniometer according to claim 1, wherein each of said sensing elements is a grid comprising two or more traces of a variable resistance material.

9. A goniometer according to claim 8, wherein said grid has an aspect ratio greater than two, wherein the primary bend axis is parallel to the shorter side and said sensing elements are in the same overlapping orientation.

10. A sensing assembly comprising:
a goniometer according to claim 1;
a flexible support means, said goniometer affixed at at least two points on the surface of said support means, wherein said goniometer forms a loop away from said surface.

11. A goniometer according to claim 1, capable of following an angle of bending to at least about 115 degrees over a finger joint.

12. A goniometer according to claim 1, wherein said electrically connecting means are capable of connecting each of said first and second strain sensing elements as two legs in a bridge circuit.

13. A goniometer capable of following an angle of bending to at least about 115 degrees, said goniometer comprising:
an inert thin electrically non-conductive flexible support backing of from 0.2 to 10 mils in thickness; and
first and second variable resistance strain sensing elements affixed on opposite sides of said backing; and
means for electrically connecting each of said elements.

14. A goniometer according to claim 13, capable of following an angle of bending to at least about 115 degrees over a finger joint.

15. A goniometer according to claim 13, wherein said electrically connecting means are capable of connecting each of said first and second strain sensing elements as two legs in a bridge circuit.

* * * * *